US012558539B2

(12) United States Patent
Gelfand et al.

(10) Patent No.: US 12,558,539 B2
(45) Date of Patent: Feb. 24, 2026

(54) DETECTING AND TREATING DISORDERED BREATHING

(71) Applicant: ZOLL RESPICARDIA, INC., Minnetonka, MN (US)

(72) Inventors: Mark Gelfand, New York, NY (US); Howard R. Levin, Teaneck, NJ (US); Andrew Halpert, Coral Springs, FL (US); Antonios Panteleon, Nea Penteli (GR)

(73) Assignee: ZOLL RESPICARDIA, INC., Minnetonka, MN (US)

( * ) Notice: Subject to any disclaimer, the term of this patent is extended or adjusted under 35 U.S.C. 154(b) by 19 days.

(21) Appl. No.: 18/220,506

(22) Filed: Jul. 11, 2023

(65) Prior Publication Data

US 2023/0347146 A1 Nov. 2, 2023

Related U.S. Application Data

(63) Continuation of application No. 17/709,555, filed on Mar. 31, 2022, now abandoned, which is a (Continued)

(51) Int. Cl.
*A61N 1/36* (2006.01)
*A61B 5/00* (2006.01)
(Continued)

(52) U.S. Cl.
CPC .......... *A61N 1/3601* (2013.01); *A61B 5/0826* (2013.01); *A61B 5/4818* (2013.01); (Continued)

(58) Field of Classification Search
CPC .. A61N 1/3601; A61N 1/3605; A61N 1/3611; A61N 1/36514; A61B 5/0826; (Continued)

(56) References Cited

U.S. PATENT DOCUMENTS

| | | | |
|---|---|---|---|
| 4,129,125 A | 12/1978 | Lester et al. | |
| 4,702,253 A | 10/1987 | Nappholz et al. | |
| | | (Continued) | |

FOREIGN PATENT DOCUMENTS

| | | |
|---|---|---|
| DE | 10103288 A1 | 8/2002 |
| WO | 2008092246 A1 | 8/2008 |

OTHER PUBLICATIONS

Aiyar, Harish et al., Diaphragm Pacing for Chronic Respiratory Insufficient, CRC Press, LLC, 2001, Chapter 9.
(Continued)

*Primary Examiner* — Pamela M. Bays
(74) *Attorney, Agent, or Firm* — Lando & Anastasi, LLP

(57) ABSTRACT

A system for treating disordered breathing of a human being includes an implantable transvenous stimulation lead having at least one stimulation electrode and a sensor configured to detect activity level of the human being. The system includes an energy source, a pulse generator and circuitry, the circuitry operative to receive a signal indicative of the activity level of the human being from the sensor, wherein the circuitry is configured to cause the energy source and the pulse generator to deliver spaced apart stimulation signals to the at least one stimulation electrode while the activity level of the human being is sufficiently low to be indicative of sleep. Spaced apart stimulation pulses from the electrode are configured to extend a duration of a time of at least one breath being defined as the time from an onset of inhalation to the onset of inhalation of a successive breath.

20 Claims, 17 Drawing Sheets

Related U.S. Application Data continuation of application No. 15/985,089, filed on May 21, 2018, now Pat. No. 11,305,114, which is a continuation of application No. 12/163,500, filed on Jun. 27, 2008, now Pat. No. 9,987,488.

(60) Provisional application No. 60/937,426, filed on Jun. 27, 2007.

(51) Int. Cl.

| | |
|---|---|
| *A61B 5/08* | (2006.01) |
| *A61B 5/0205* | (2006.01) |
| *A61B 5/091* | (2006.01) |
| *A61B 5/113* | (2006.01) |
| *A61N 1/05* | (2006.01) |
| *A61N 1/365* | (2006.01) |

(52) U.S. Cl.
CPC .......... *A61N 1/3605* (2013.01); *A61N 1/3611* (2013.01); *A61B 5/0205* (2013.01); *A61B 5/0816* (2013.01); *A61B 5/091* (2013.01); *A61B 5/113* (2013.01); *A61B 5/4836* (2013.01); *A61N 1/0551* (2013.01); *A61N 1/36139* (2013.01); *A61N 1/36514* (2013.01)

(58) Field of Classification Search
CPC ... A61B 5/4818; A61B 5/0205; A61B 5/0816; A61B 5/113
See application file for complete search history.

(56) References Cited

U.S. PATENT DOCUMENTS

| | | | |
|---|---|---|---|
| 4,827,935 A | 5/1989 | Geddes et al. | |
| 4,830,008 A | 5/1989 | Meer | |
| 5,002,067 A | 3/1991 | Berthelsen et al. | |
| 5,056,519 A | 10/1991 | Vince | |
| 5,146,918 A | 9/1992 | Kallok et al. | |
| 5,170,802 A | 12/1992 | Mehra | |
| 5,199,428 A | 4/1993 | Obel et al. | |
| 5,265,604 A | 11/1993 | Vince | |
| 5,330,507 A | 7/1994 | Schwartz | |
| 5,423,865 A | 6/1995 | Bowald et al. | |
| 5,483,969 A | 1/1996 | Testerman et al. | |
| 5,485,851 A | 1/1996 | Erickson | |
| 5,524,632 A | 6/1996 | Stein et al. | |
| 5,540,734 A | 7/1996 | Zabara | |
| 5,578,061 A | 11/1996 | Stroetmann et al. | |
| 5,922,014 A | 7/1999 | Warman et al. | |
| 5,938,694 A | 8/1999 | Jaraczewski et al. | |
| 6,006,134 A | 12/1999 | Hill et al. | |
| 6,132,384 A | 10/2000 | Christopherson et al. | |
| 6,212,435 B1 | 4/2001 | Lattner et al. | |
| 6,266,564 B1 | 7/2001 | Hill et al. | |
| 6,314,324 B1 | 11/2001 | Lattner et al. | |
| 6,360,740 B1 | 3/2002 | Ward et al. | |
| 6,415,183 B1 | 7/2002 | Scheiner et al. | |
| 6,449,507 B1 | 9/2002 | Hill et al. | |
| 6,463,327 B1 | 10/2002 | Lurie et al. | |
| 6,532,388 B1 | 3/2003 | Hill et al. | |
| 6,537,228 B1 | 3/2003 | Lambert | |
| 6,542,774 B2 | 4/2003 | Hill et al. | |
| 6,587,726 B2 | 7/2003 | Lurie et al. | |
| 6,589,188 B1 | 7/2003 | Street et al. | |
| 6,641,542 B2 | 11/2003 | Cho et al. | |
| 6,684,101 B2 | 1/2004 | Daum | |
| 6,718,208 B2 | 4/2004 | Hill et al. | |
| RE38,705 E | 2/2005 | Hill et al. | |
| 6,881,192 B1 | 4/2005 | Park | |
| 6,890,306 B2 | 5/2005 | Poezevera | |
| 6,928,324 B2 | 8/2005 | Park et al. | |
| 6,934,583 B2 | 8/2005 | Weinberg et al. | |
| 6,937,903 B2 | 8/2005 | Schuler et al. | |
| 6,964,641 B2 | 11/2005 | Cho et al. | |
| 7,025,730 B2 | 4/2006 | Cho et al. | |
| 7,070,568 B1 | 7/2006 | Koh | |
| 7,077,132 B2 | 7/2006 | Berthon-Jones | |
| 7,082,331 B1 | 7/2006 | Park et al. | |
| 7,094,207 B1 | 8/2006 | Koh | |
| 7,155,278 B2 | 12/2006 | King et al. | |
| 7,179,229 B1 | 2/2007 | Koh | |
| 7,184,829 B2 | 2/2007 | Hill et al. | |
| 7,200,442 B1 | 4/2007 | Koh et al. | |
| 7,212,862 B2 | 5/2007 | Park et al. | |
| 7,223,244 B1 | 5/2007 | Koh | |
| 7,225,019 B2 | 5/2007 | Jahns et al. | |
| 7,225,021 B1 | 5/2007 | Park et al. | |
| 7,245,971 B2 | 7/2007 | Park et al. | |
| 7,269,457 B2 | 9/2007 | Shafer et al. | |
| 7,269,459 B1 | 9/2007 | Koh | |
| 7,277,757 B2 | 10/2007 | Casavant et al. | |
| 7,340,302 B1 * | 3/2008 | Falkenberg .......... | A61N 1/3611 607/9 |
| 7,357,775 B1 | 4/2008 | Koh | |
| 7,361,146 B1 | 4/2008 | Bharmi et al. | |
| 7,363,086 B1 | 4/2008 | Koh et al. | |
| 7,371,220 B1 | 5/2008 | Koh et al. | |
| 7,454,250 B1 * | 11/2008 | Bjorling .............. | A61N 1/3601 607/42 |
| 7,467,012 B1 * | 12/2008 | Park ....................... | A61N 1/056 600/483 |
| 7,813,805 B1 | 10/2010 | Farazi | |
| 9,987,488 B1 | 6/2018 | Gelfand et al. | |
| 10,603,491 B1 | 3/2020 | Gelfand et al. | |
| 2001/0003799 A1 | 6/2001 | Boveja | |
| 2002/0049479 A1 | 4/2002 | Pitts | |
| 2002/0128563 A1 | 9/2002 | Carlson et al. | |
| 2003/0078623 A1 | 4/2003 | Weinberg et al. | |
| 2003/0088244 A1 | 5/2003 | Swanson et al. | |
| 2003/0135248 A1 | 7/2003 | Stypulkowski | |
| 2003/0153953 A1 * | 8/2003 | Park ................... | A61N 1/36585 607/17 |
| 2003/0195571 A1 | 10/2003 | Burnes et al. | |
| 2003/0199945 A1 * | 10/2003 | Ciulla ................ | A61N 1/36003 607/48 |
| 2005/0043765 A1 | 2/2005 | Williams et al. | |
| 2005/0043772 A1 | 2/2005 | Stahmann et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0165457 A1 | 7/2005 | Benser et al. | |
| 2005/0197588 A1 | 9/2005 | Freeberg | |
| 2005/0234518 A1 * | 10/2005 | Heruth ................. | A61B 5/1118 600/509 |
| 2005/0240240 A1 | 10/2005 | Park et al. | |
| 2005/0288729 A1 | 12/2005 | Libbus et al. | |
| 2006/0030894 A1 | 2/2006 | Tehrani | |
| 2006/0036294 A1 | 2/2006 | Tehrani | |
| 2006/0084060 A1 | 4/2006 | Nagahama et al. | |
| 2006/0122662 A1 * | 6/2006 | Tehrani ................. | A61B 5/395 607/42 |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0190052 A1 | 8/2006 | Yun et al. | |
| 2006/0229677 A1 | 10/2006 | Moffitt et al. | |
| 2006/0247729 A1 | 11/2006 | Tehrani et al. | |
| 2007/0021795 A1 | 1/2007 | Tehrani | |
| 2007/0118183 A1 | 5/2007 | Gelfand et al. | |
| 2007/0156199 A1 | 7/2007 | Koh et al. | |
| 2007/0260285 A1 | 11/2007 | Libbus et al. | |
| 2008/0154330 A1 | 6/2008 | Tehrani et al. | |
| 2008/0161878 A1 | 7/2008 | Tehrani et al. | |
| 2008/0167695 A1 | 7/2008 | Tehrani et al. | |
| 2008/0177347 A1 | 7/2008 | Tehrani et al. | |
| 2008/0183239 A1 | 7/2008 | Tehrani et al. | |
| 2008/0183240 A1 | 7/2008 | Tehrani et al. | |
| 2008/0183254 A1 | 7/2008 | Bly et al. | |
| 2008/0183259 A1 | 7/2008 | Bly et al. | |

(56) References Cited

U.S. PATENT DOCUMENTS

| | | | |
|---|---|---|---|
| 2008/0183264 A1 | 7/2008 | Bly et al. | |
| 2008/0188903 A1 | 8/2008 | Tehrani et al. | |
| 2008/0188904 A1 | 8/2008 | Tehrani et al. | |
| 2008/0234694 A1 | 9/2008 | Stegfeldt et al. | |
| 2009/0088827 A1 | 4/2009 | Tockman et al. | |
| 2010/0249630 A1 | 9/2010 | Droitcour et al. | |
| 2011/0060380 A1 | 3/2011 | Gelfand et al. | |
| 2018/0326209 A1 | 11/2018 | Gelfand et al. | |
| 2022/0218989 A1 | 7/2022 | Gelfand et al. | |
| 2025/0082933 A1 | 3/2025 | Gelfand et al. | |

OTHER PUBLICATIONS

Arzt, Michael et al., Treatment of Sleep Apnea in Heart Failure, Am J Respir Crit Care Med vol. 173, pp. 1300-1308, 2006.

Bilgutay, A.M. et al., Augmented Ventilation by Synchronous Phrenic Nerve Stimulation, Trans. Amer. Soc. Artif. Int. Organs, 1970, vol. XVI, pp. 213-217.

Brack, Thomas, Cheyne-Stokes Respiration in Patients with Congestive Heart Failure, Swiss Med Wkly 2003; 133:605-610, www.smw.ch.

Caples, Sean M. et al., Influence of Cardiac Function and Failure on Sleep-Disordered Breathing, Journal of Applied Physiology 2006, vol. 100, pp. 11-12.

Chatfield, Paul O. et al., Role of Pulmonary Proprioceptive Reflexes in Suppression of Spontaneous Breathing During Electrophrenic Respiration, Dept. of Physiology, Harvard Medical School, and Dept. of Physiology, Harvard School of Public Health, 1950, vol. 163.

Diedrichs, Helger et al., Symptomatic Relief Precedes Improvement of Myocardial Blood Flow in Patients Under Spinal Cord Stimulation, BioMed Central, 2005, pp. 1-7.

Dobelle, William H., Use of Breathing Pacemakers to Suppress Intractable Hiccups of up to Thirteen Years Duration, ASAIO Journal 1999, pp. 524-525.

Escher, Doris J.W., Clinical control of Respiration by Transvenous Phrenic Pacing, Trans. Amer. Soc. Artif. Int. Organs., vol. XIV, 1968.

Esler, Murray et al., Is Obstructive Sleep Apnea the Cause of Sympathetic Nervous Activation in Human Obsesity?, Journal of Applied Physiology 2006, vol. 100, pp. 11-12.

Furman, Seymour, MD et al., Transvenous Stimulation of the Phrenic Nerves, Journal of Thoracic and Cardiovascular Surgery, vol. 62, No. 5, 1971, pp. 743-751.

Garrido-Garcia, H et al., Treatment of Chronic Ventilatory Failure Using a Diaphragmatic Pacemaker, Spinal Cord (1998) 36, 310-314.

Gottfried, Stewart B. et al., Effects of Phrenic Stimulation on Upper Airway Resistance in Anethetized Dogs, Am Physiological Society 1983, 0161-7567/83, pp. 419-426.

Hall, Michael J. et al., Cycle Length of Periodic Breathing in Patients with and without Heart Failure, Am. J. Respir. Crit. Care Med vol. 154, pp. 376-381, 1996.

Handa, Y. et al., Basic Studies on Electrophrenic Respiration Part 2—Assisted Ventilation by the Synchronous Electrophrenic Respirator, Medical and Biological Engineering, Jul. 1976.

Hasdemir, Can MD et al., Jpn Heart J, vol. 44 No. 3, 2003.

Ishii, Kiyoshi, Effects of Bilateral transvenous diaphrahm pacing on hemodynamic function in patients after cariac operations, 1990.

Javaheri, Shahrokh M.D., CPAP Should Not Be Used for Central Sleep Apnea in Congestive Heart Failure Patients, Journal of Clinical Sleep Medicine, vol. 2, No. 4, 2006.

Javaheri, Shahrokh, MD, Acetazolamide Improves Central Sleep Apnea in Heart Failure Pulmonary Service, Department of Veterans Affairs Medical Center, and Department of Medicine, University of Cincinnati College of Medicine, Cincinnati, Ohio Am J Respir Crit Care Med vol. 173, pp. 234-237, 2006, Jul. 5, 2005.

Javaheri, Shahrokh, MD, Central Sleep Apnea in Congestive Heart Failure: Prevalence, Mechanisms, Impact, and Therapeutic Options, Seminars in Respiratory and Critical Care Medicine, 2005, vol. 26, No. 1.

Kaneko, S. et al., A New Approach to Respiratory Assist for Phrenic Nerve Paralysis, Trans Am Soc. Artif Intern Organs, 1985, vol. XXXI, pp. 301-304.

Kimura, M. et al. Heart Rate and Body Tempurature Sensitive Diaphragm Pacing, Med. & Biol. Eng. & Comput. 1992, 30, 155-161.

Kimura, M. et al., A Heart-Rate-Responsive Diaphragm Pacemaker, Med. & Biol. Eng. & Comput., 1987, 25, 458-462.

Kimura, M. et al., Addition to an RF-Coupled Phrenic Nerve Stimulator Implant to Provide Outward Transmission of Body Temperature, Med. & Biol. Eng. & Comput. 1986, 24, 659-661.

Kingma, John G. Jr. et al., Neuromodulation Theraphy Does Not Influence Blood Flow Distribution or Left-Ventricular Dynamics During Acute Muocardial Ischemia, Autonomic Neuroscience: Basic and Clinical 91 (2001) pp. 47-54.

Kohnlein, T. et al., Central Sleep Apnea Syndrome in Patients with Chronic Heart Disease: A Critical Review of the Current Literature, Thorax 2002; 57:547-554.

Leuenberger, Urs A. et al., Hypoxia Augments Apnea-Induced Peripheral Vasoconstruction in Humans, Journal of Applied Physiology 2001, vol. 90, pp. 1516-1522.

Leung, Richard S. T. et al., Influence of Cheyne-Stokes Respiration on Cariovascular Oscillations in Heart Failure, Am J Respir Crit Care Med, 2003, vol. 167. pp 1534-1539.

Levy, T. et al., A Comparison Between Passive and Active Fixation Leads in the Coronary Sinus for Biatrial Pacing, The European Society of Cardiology 2000.

Linderoth, Bengt, MD, Pho et al., Mechanisms of Spinal Cord Stimulation in Painful Syndromes: Role of Animal Models, American Academy of Pain Medicine, vol. 7, No. S14-S26, 2006.

Lorenzi-Filho, Geraldo et al., Cheyne-Stokes Respiration in Patients with Congestive Heart Failure: Causes and Consequences, Clinics 2005; 60(4):333-44.

Macintyre, Neil R., MD, Setting the Frequency-Tidal vol. Pattern, ww.rcjournal.com/contents/03.02/03.02.0266.asp. [retrieved Sep. 11, 2006].

Oliven, Arie et al., Upper Airway Response to Electrical Stimulation of the Genioglossus in Obstructive Sleep Apnea, Journal of Applied Physiology, 95:2023-2029, 2003.

Oliven, Arie, et al., Upper Airway Response to Electrical Stimulation of the Genioglossus in Obstructive Sleep Apnea, Journal of Applied Physiology 2003, vol. 95, pp. 2023-2029.

Parati, Gianfranco et al., Sleep Apnea: Epidemiology, Pathphysiology, and Relation to Cardiovascular Risk, Am Journal Physiological Society 2007, vol. 293, pp. R1671-R1683.

Planas, Roque F. et al., Diaphragmatic Pressures: Transvenous vs. Direct Phrenic Nerve Stimulation, Am Physiological Society 1985, 0161-7567/85, pp. 269-273.

Plisiene, Jurgita et al., Selective Transvascular Stimulation of Cardiac Autonomic Nerves: A Novel Technique, Biomedicine vol. 2 No. 1, Jul. 2002.

Punjabi, Naresh M. et al., Disorders of Glucose Metabolism in Sleep Apnea, Journal of Applied Physiology 2005, vol. 99, pp. 1998-2007.

Redline, Susan et al., Beyond the Fat Boy, Journal of Applied Physiology 2005, vol. 99: pp. 1243-1244.

Sarnoff, Stanley J. et al., Electrophrenic Respiration IV. The Effectiveness of Contralaterial Ventilation during Activity of One Phrenic Nerve, Dept. of Physiology, Harvard School of Public Health, 1949, pp. 929-937.

Sarnoff, Stanley J. et al., Electrophrenic Respiration. III. Mechanism of the Inhibition of Spontaneous Respiration, Dept. of Physiology, Harvard School of Public Health, 1948, vol. 155, pp. 203-207.

Schauerte, Patrick et al., Catheter Stimulation of Cardiac Parasympathetic Nerves in Humans: A Novel Approach to the Cariac Autonomic Nervous System, American Heart Association 2006.

Series, F. et al., Site of Phrenic Nerve Stimulation-Induced Upper Airway Collapse: Influence of Expiratory Time, Journal of Applied Physiology 2002, vol. 92, pp. 665-671.

(56) References Cited

OTHER PUBLICATIONS

Series, Frederic, Assessment of Upper Airway Dynamics in Awake Patients with Sleep Apnea Using Phrenic Nerve Stimulation, Am Journal Respir Crit Care Med, 2000, vol. 162., pp. 795-800.

Shaul, Donal B., et al., Thoracoscopic Placement of Phrenic Nerve Electrodes for Diaphragmatic Pacing in Children, Journal of Pediatric Surgery, vol. 37, No. 7 pp. 974-978, 2002.

Stemmer, Edward A. MD et al., Diaphragmatic Pacing in the Treatment of Hypoventilation Syndrome, Journal of Thoracic and Cardiovascular Surgery, vol. 54, No. 5, 1967, pp. 649-657.

Taira, Takaomi, MD, Ph. D. et al., Phrenic Nerve Stimulation for Diaphragm Pacing with a Spinal cord Stimulator, Elsevier Science, Surg Neurol, 2003; 59:128-32.

Tanaka, Satoshi et al., Mechanims of Sustained Cutaneous Vasodilation Induced by Spinal Cord Stimulation, Autonomic Neuroscience: Basic and Clinical 114 (2004) pp. 55-60.

Thoma, H. et al., The Vienna Phrenic Pacemaker, Longterm Data of Failures, 1993.

Vaseghi, et al., Beyond Coronary Sinus Angiography: The Value of Coronary Arteriography and Identification of the Pericardiophrenic Vein During Left Ventricular Lead Placement, PACE, 2005, vol. 28.

Yasuma, Fumihiko et al., Eight-Year Follow-Up Study of a Patient with Central Alveolar Hypoventilation Treated with Diaphragm Pacing, Respiration, 1998; 65:313-316.

Yuminco, Dai et al., Central Sleep Apnea and Cheyne-Stokes Respiration, Proceedings of the American Thoracic Society, 2008, vol. 5, pp. 226-236.

* cited by examiner

Figure 7

DETECTING AND TREATING DISORDERED BREATHING

CROSS REFERENCE TO RELATED APPLICATIONS

This application claims the benefit under 35 U.S.C. § 120 as a continuation of U.S. application Ser. No. 17/709,555, filed Mar. 31, 2022, titled "DETECTING AND TREATING DISORDERED BREATHING," which claims the benefit under 35 U.S.C. § 120 as a continuation of U.S. application Ser. No. 15/985,089, filed May 21, 2018, titled "DETECTING AND TREATING DISORDERED BREATHING," now U.S. Pat. No. 11,305,114, which claims the benefit under 35 U.S.C. § 120 as a continuation of U.S. application Ser. No. 12/163,500, filed Jun. 27, 2008, titled "DETECTING AND TREATING DISORDERED BREATHING," now U.S. Pat. No. 9,987,488, which claims priority under 35 U.S.C. § 119(e) to U.S. Provisional Application Ser. No. 60/937,426, filed Jun. 27, 2007, titled "ALGORITHMS FOR PHRENIC NERVE STIMULATION," each of which is hereby incorporated herein by reference in its entirety for all purposes.

FIELD OF THE INVENTION

The present invention relates to detecting and treating defects in human respiration, particularly the types of disordered breathing that may accompany heart disease.

BACKGROUND

Human respiration is an extraordinarily complicated process. Although rhythmic breathing, inhalation and exhalation, is familiar to all of us, the underlying processes that give rise to the observed respiration cycle are complex. In general respiration permits gas exchange between gases in the blood and gases in the environment. In a healthy individual, oxygen is provided to the blood and carbon dioxide, which is a product of metabolic processes in the body, is driven off into the atmosphere. Respiration is subject to both voluntary and involuntary control and several disease processes can have a profound impact on respiration.

A person's respiration is controlled by the autonomic nervous system that integrates inputs from many physiologic sensors such as mechanoreceptors and chemoreceptors. The central nervous system commands the diaphragm and other muscles in the chest as well as in the neck to phasically contract and relax thus producing a breath of certain shape and tidal volume. It also acts as a respiratory pacemaker by setting the breathing rate. In a normal sleeping person the next breath is typically initiated substantially immediately after the previous breath is completely exhaled. The term tidal volume refers to the volume of air inspired or expired during a respiratory cycle. Together tidal volume and breathing rate determine minute volume of ventilation that determines the rate at which oxygen is delivered and $CO_2$ is removed from the respiratory system.

The term disordered breathing is used herein to describe a variety of observable respiration patterns that deviate from normal respiration. For example, Cheyne-Stokes respiration ("CSR") is clinically observed and declared when a patient has bouts of "rapid" and/or "deep" breathing followed by reductions in breathing or apnea-hypopnea. This abnormal pattern of breathing can be seen in patients with strokes, traumatic brain injuries, brain tumors, and congestive heart failure and is usually a result of poor control of blood gas chemistry by the central nervous system.

"Pure" Cheyne-Stokes respiration is also called central sleep apnea by the medical community and is sometimes present with congestive heart failure. However, CSR breathing may be mixed with other respiration disorders that may or may not be related to congestive heart failure or other cardiac disorders.

SUMMARY

Embodiments in accordance with the present invention are directed to detecting and treating disordered breathing. In some embodiments, a device may operate by sensing natural respiration and phasically synchronizing the delivery of a stimulus with the breath after inspiration. The stimulation of these embodiments is provided to at least one half of a patient's phrenic nerves which innervate one side of the diaphragm associated with one lung. The stimulus is of a sufficient character to cause that lung to "be still," with some amount of air retained in the lung, and lung volume generally will not change during the stimulation, within some broadly defined limits. It is the belief of the inventors that it may be sufficient to stimulate and still only one lung under the theory that compensatory physiologic feedback mechanisms preserved on the unstimulated lung of the central and autonomic nervous system will interact in a virtuous and favorable way with the stimulation regime to provide the therapy.

It is believed that arresting at least one lung will prolong breaths and thus temporarily slow respiration and modify or modulate the tidal volume of breathing. This reduction of tidal volume may prevent blood carbon dioxide from being driven to low levels associated with apnea.

In other embodiments in accordance with the present invention, the stimulus is applied to still at least one lung upon detection of an apnea-hypopnea of some length or upon the detection of hyperpnea. In these embodiments, the stimulation may be initiated during the apnea-hypopnea period or upon detection of a breath of a predetermined intensity near the end of apnea-hypopnea. The stimulation may be initiated in phase with respiration or irrespective of the phase of respiration. If initiated irrespective of the phase of respiration, the stimulation may be gradually increased in intensity so as to expand and still at least one lung slowly so as not to disturb or arouse a sleeping patient. For purposes of this discussion, hyperpnea is defined as abnormally rapid or deep breathing. In some but not all cases, hyperpnea may involve rapid breathing that is compensating for the reduced respiratory effectiveness of a previous period of apnea-hypopnea or reduced breathing.

Embodiments in accordance with the present invention may cooperate with naturally occurring physiologic feedback mechanisms to provide a therapy for disordered breathing. In one embodiment, a fully implanted device coupled to a transvenous lead system may be provided to monitor breathing and extract inspiration points, expiration points and other data associated with a physiologic breathing pattern. A programmable computer may be provided with control software for managing both the respiration measuring system as well as extracting useful data concerning breathing. The programmable computer may be described as a combination of circuitry and software, circuitry and firmware, or a computer with software or firmware, and all of these descriptions contemplate the same essential elements. The control software within the device may select the timing for the delivery of hemi diaphragmatic stimulation and accept input information from a variety of sources that can be used in nested control loops to tailor the therapy to a particular patient and to provide a different therapy as the patient's needs change. In one embodiment in accordance with the invention, a system for treating disordered breathing includes a stimulation lead having a stimulation electrode, a respiration sensor, an energy source, a pulse generator, and circuitry. In this embodiment, the circuitry is operative to monitor signals from the respiration sensor and detect apnea-hypopnea. The circuitry will deliver a stimulation signal to the stimulation electrode after the detection of apnea-hypopnea. In this embodiment, the stimulation signal has a duration of at least ten seconds.

In another embodiment in accordance with the invention, a system for treating disordered breathing includes a stimulation lead having a stimulation electrode, a respiration sensor, an energy source, a pulse generator, and circuitry. In this embodiment, the circuitry is operative to monitor signals from the respiration sensor and detect apnea-hypopnea. The circuitry will deliver a stimulation pulse to the stimulation electrode after the detection of a hyperpnea following apnea-hypopnea. In this embodiment, the stimulation signal has a duration of at least ten seconds.

In yet another embodiment in accordance with the invention, a system for treating disordered breathing includes a stimulation lead having a stimulation electrode, a respiration sensor, an energy source, a pulse generator, and circuitry. In this embodiment, the circuitry is operative to monitor signals from the respiration sensor and detect apnea-hypopnea by accumulating data from the respiration sensor to determine a value representative of average tidal volume and then detecting hyperpnea when, for example, the measured value is below 30% of the average value for ten seconds. The circuitry will deliver a stimulation pulse to the stimulation electrode after the detection of apnea-hypopnea. In this embodiment, the stimulation signal has a duration of at least ten seconds.

In yet another embodiment in accordance with the invention, a system for treating disordered breathing includes a stimulation lead having a stimulation electrode, a respiration sensor, an energy source, a pulse generator, and circuitry. In this embodiment, the circuitry is operative to monitor signals from the respiration sensor and detect apnea-hypopnea by accumulating data from the respiration sensor to determine a value representative of average tidal volume and then detecting hyperpnea when the measured value is below 30% of the average value for ten seconds. The circuitry will then detect hyperpnea when the value representative of tidal volume exceeds 30% of the average value after the detection of apnea-hypopnea. The circuitry will deliver a stimulation pulse to the stimulation electrode after the detection of hyperpnea following apnea-hypopnea. In this embodiment, the stimulation signal has a duration of at least ten seconds.

In another embodiment in accordance with the invention, a system for treating disordered breathing includes a stimulation lead having a stimulation electrode, a respiration sensor, an energy source, a pulse generator, and circuitry. In this embodiment the stimulation lead is configured to be implanted in a blood vessel proximate a phrenic nerve in a patient. In this embodiment, the circuitry is operative to monitor signals from the respiration sensor and detect apnea-hypopnea. The circuitry will deliver a stimulation pulse to the stimulation electrode after the detection of apnea-hypopnea. In this embodiment, the stimulation signal has a duration of at least ten seconds.

A system for treating disordered breathing in accordance with embodiments of the invention includes a stimulation lead having a stimulation electrode, a respiration sensor, an energy source, a pulse generator, and circuitry. The circuitry of this embodiment is operative to determine the onset of a hyperpnea based on the respiration sensor signals and deliver a stimulation signal to the stimulation electrode during hyperpnea, the signal having a duration of at least one second to extend the duration of the breath.

Another system for treating disordered breathing in accordance with embodiments of the invention includes a stimulation lead having a stimulation electrode, a respiration sensor, an energy source, a pulse generator, and circuitry. The system receives signals from the respiration sensor and calculates a baseline breath duration. The circuitry of this embodiment is operative to determine the onset of a hyperpnea based on the respiration sensor signals and deliver a stimulation signal to the stimulation electrode during hyperpnea, the signal having a duration of at least 25% of the baseline breath duration.

Another system for treating disordered breathing in accordance with embodiments of the invention includes a stimulation lead having a stimulation electrode, a respiration sensor, an energy source, a pulse generator, and circuitry. The circuitry of this embodiment is operative to determine the onset of a hyperpnea and the peak of inspiration based on the respiration sensor signals and deliver a stimulation signal to the stimulation electrode during hyperpnea proximate the peak of inspiration, the signal having a duration of at least one second to extend the duration of the breath.

A system for treating disordered breathing in accordance with embodiments of the invention includes a stimulation lead having a stimulation electrode, a respiration sensor, an energy source, a pulse generator, and circuitry. The circuitry of this embodiment is operative to determine the onset of a hyperpnea based on the respiration sensor signals and to determine the duration of a hyperpnea cycle and deliver a stimulation signal to the stimulation electrode during hyperpnea, the signal having a duration greater than 25% of the duration of the hyperpnea cycle. Another system for treating disordered breathing in accordance with embodiments of the invention includes a stimulation lead having a stimulation electrode, a respiration sensor, an energy source, a pulse generator, and circuitry. The circuitry of this embodiment is operative to determine the onset of a hyperpnea based on the respiration sensor signals and to determine the duration of a hyperpnea cycle. The circuitry is also operative to deliver a stimulation signal to the stimulation electrode during hyperpnea, the signal being initiated after the midpoint of the hyperpnea cycle and having a duration of at least one second to extend the duration of the breath. In some variations of this embodiment the signal is initiated proximate the peak of inspiration of a breath that occurs after the midpoint of hyperpnea.

Another system for treating disordered breathing in accordance with embodiments of the invention includes a stimulation lead having a stimulation electrode, a respiration sensor, an energy source, a pulse generator, and circuitry. The circuitry of this embodiment is operative to determine the onset of a hyperpnea based on the respiration sensor signals and to determine the duration of a hyperpnea cycle. The circuitry is also operative to deliver a stimulation signal to the stimulation electrode during hyperpnea, the signal being initiated after the midpoint of the hyperpnea cycle and having a duration of at least one second to extend the duration of the breath. The circuitry of this embodiment is also operative to deliver a stimulation signal at the peak of inspiration for several breaths beginning after the midpoint of hyperpnea.

Another system for treating disordered breathing in accordance with embodiments of the invention includes a stimulation lead having a stimulation electrode, a respiration sensor, an energy source, a pulse generator, and circuitry. The circuitry of this embodiment is operative to determine the onset of a hyperpnea based on the respiration sensor signals. The circuitry is also operative to deliver at least three segmented stimulation signals to the stimulation electrode during the hyperpnea.

Another system for treating disordered breathing in accordance with embodiments of the invention includes a stimulation lead having a stimulation electrode, a respiration sensor, an energy source, a pulse generator, and circuitry. The circuitry of this embodiment is operative to determine the onset of a hyperpnea based on the respiration sensor signals and to determine the average duration of a hyperpnea cycle and the average duration of an apnea-hypopnea cycle. The circuitry is also operative to deliver a stimulation signal to the stimulation electrode during hyperpnea based on the average duration of a hyperpnea cycle and establish a blanking period based on the average duration of an apnea-hypopnea cycle.

A system for treating disordered breathing in accordance with embodiments of the invention includes a stimulation lead having a stimulation electrode, a respiration sensor, an energy source, a pulse generator, and circuitry. The circuitry of this embodiment is operative to determine the onset of a hyperpnea based on the respiration sensor signals and deliver a stimulation signal to the stimulation electrode during hyperpnea, where the signal has a duration of at least one second and is in the form of a gradually rising and descending pulse train envelope.

In another embodiment in accordance with the invention, a method of monitoring or treating disordered breathing includes calculating an average duration of a patient's hyperpnea over some period of time and stimulating a diaphragm of the patient upon detection of hyperpnea. In this embodiment the stimulation lasts at least 30% as long as the calculated average duration of hyperpnea.

Another embodiment in accordance with the invention involves a method of monitoring or treating disordered breathing. The method includes gathering data related to a patient's breathing and generating a value representative of the tidal volume of the breaths of the patient. The tidal volumes of sequential breaths are compared and hyperpnea is detected when there are three sequential breaths where the tidal volume of each breath is at least 20% greater than the tidal volume of the previous breath. The method of this embodiment includes calculating an average duration of a patient's hyperpnea over some period of time and stimulating a diaphragm of the patient upon detection of hyperpnea. In this embodiment the stimulation lasts at least 30% as long as the calculated average duration of hyperpnea.

In another embodiment in accordance with the invention, a method of monitoring or treating disordered breathing includes calculating an average duration of a patient's hyperpnea over some period of time and stimulating a diaphragm of the patient upon detection of hyperpnea. In this embodiment the stimulation lasts at least 30% as long as the calculated average duration of hyperpnea. The stimulation signal of this embodiment is in the form of a gradually rising and descending pulse train envelope. Some examples of possible pulse train shapes include linear, parabolic, and elliptical.

In yet another embodiment in accordance with the invention, a method of monitoring or treating disordered includes calculating an average duration of a patient's episodes of hyperpnea over some period of time and an average midpoint of the hyperpnea episode and stimulating a diaphragm of the patient during hyperpnea after the midpoint of the hyperpnea.

In yet another embodiment in accordance with the invention, a method of monitoring or treating disordered includes calculating an average duration of a patient's episodes of hyperpnea over some period of time and an average midpoint of the hyperpnea episode and stimulating a diaphragm of the patient during hyperpnea after the midpoint of the hyperpnea. This embodiment includes determining the peak of inspiration and stimulating proximate the peak of inspiration.

In yet another embodiment in accordance with the invention, a method of monitoring or treating disordered includes calculating an average duration of a patient's episodes of hyperpnea over some period of time and an average midpoint of the hyperpnea episode and stimulating a diaphragm of the patient during hyperpnea after the midpoint of the hyperpnea. In this embodiment additional future breaths extending beyond the normal duration of hyperpnea are stimulated.

BRIEF DESCRIPTION OF THE DRAWINGS

FIG. 7 is a flowchart of a detection and treatment protocol.

DETAILED DESCRIPTION

Figure 1:
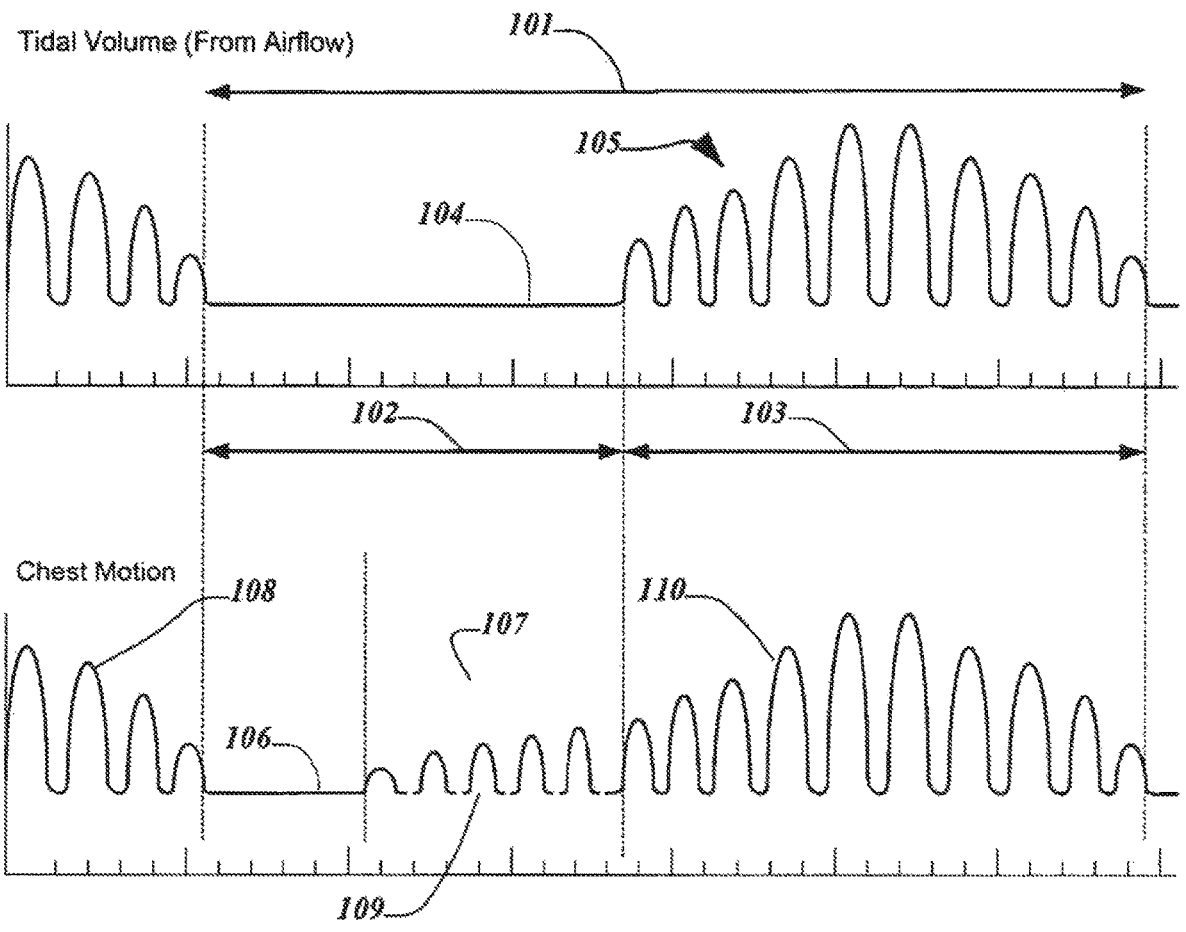
FIG. 1 is a stylized representation of tidal volume and chest motion over time of a patient.

Turning now to the Figures, FIG. 1 is a stylized representation of tidal volume and chest motion over time of a patient suffering from mixed apnea within Cheyne-Stokes Respiration. The CSR cycle 101 consists of an apnea-hypopnea period 102 and a hyperpnea period 103. During apnea-hypopnea 102 there is substantially no airflow 104 inspired or expired. During hyperpnea 103 airflow gradually increases, crests and then decreases from breath to breath. This pattern is often described as a crescendo-decrescendo pattern. In the beginning of apnea-hypopnea 106 there is no respiratory drive from the autonomic nervous system of the patient and consequently no substantial diaphragm or chest motion. This is an example of true or pure central sleep apnea. It may be caused by the suppression of drive to breathe caused by the concentration of $CO_2$ in the blood ("$PaCO_2$") crossing below an apnic threshold. This abnormally low $PaCO_2$ is likely a result of the preceding hyperpnea 108 that is in turn a manifestation of a ventilatory overshoot.

Respiratory or ventilatory overshoot describes an excessive response of the physiologic respiratory control system to a sensed change of blood gas composition. In some disordered breathing patients, poor blood flow to the brain causes the central nervous system to perceive $CO_2$ levels in the blood that are no longer representative of the overall blood $CO_2$ level. In the case of high sensed $CO_2$ levels, the central nervous system triggers an increase in respiration in response to the high sensed $CO_2$ levels, but by the time the chemoreceptors sense the reduced $CO_2$ level and begin slowing respiration, the $CO_2$ levels have already become too low. The $CO_2$ levels may drop below an apnic threshold and as a result respiration may stop or become reduced for a time. $CO_2$ levels increase during this period of reduced respiration and the cycle of overcorrection of blood gas composition continues or becomes worse. Respiratory overshoot is manifested as excessive minute ventilation or hyperpnea that leads to apnea-hypopnea within the CSR cycle.

Later in the cycle, the patient's respiratory drive is restored 109 by the increasing blood $PaCO_2$. Chest motion 109 indicates the presence of respiratory drive, but the patient is breathing against the closed airway. No airflow is present. This is obstructive apnea within the same CSR cycle. Later in the cycle the patient's airway opens 110 and chest motion is accompanied by airflow. The natural control system of the respiration in the patient overreacts to the prolonged apnea-hypopnea. Breathing gradually becomes deeper. This is a new cycle of hyperpnea. Excessive escalation of breathing control is the manifestation of another respiratory overshoot.

Figure 2:
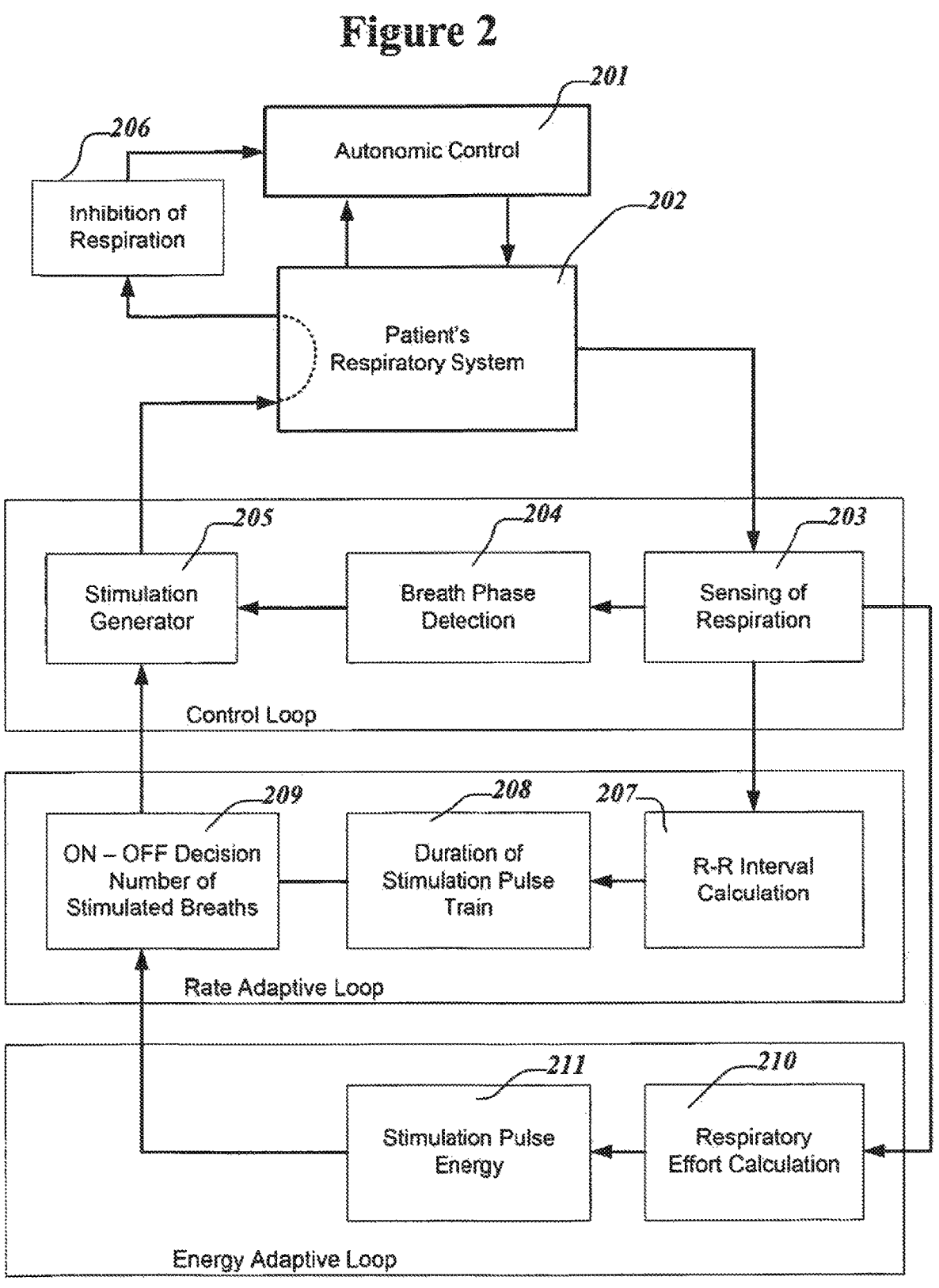
FIG. 2 is a representation of a system as it interacts with a patient's respiratory system.

FIG. 2 is a representation of a system in accordance with embodiments of the invention as it interacts with a patient's respiratory system. A patient's respiration is monitored 203 by a respiratory sensor that can be, for example, an impedance sensor, a pressure sensor or an accelerometer. A respiratory waveform can be acquired and stored in the system memory. Embedded software analyzes the waveform 204 and detects parameters of a breath such as the breath phase (inspiration or expiration) and tidal volume. At the appropriate time in the breath cycle, such as for example the end of inspiration, a pulse train or signal of stimulation is applied by the stimulation generator 205 to a phrenic nerve. In this embodiment, the pulse train is of sufficient energy to keep one hemidiaphragm muscle contracted (somewhat flattened) thus trapping some amount of air in at least one lung of the patient's respiratory system 202. This pattern of stimulation results in the inhibition of respiration 206 that may temporarily prevent the natural respiratory pacemaker 201 of the patient from initiating a new breath. It is believed that this may be at least partially accomplished via a vagal feedback into the autonomic control 201 system of the patient from the stretch receptors (mechanoreceptors) of the lung. As a result, the breathing rate of the patient is momentarily reduced. This reduction results in the suppression of respiratory overshoot that would otherwise be caused by the unstable autonomic control. Prevention or reduction of the overshoot may prevent $PaCO_2$ from dropping below the apnic threshold. This may prevent the cessation or clinically undesirable reduction of breathing during the apnea-hypopnea phase of the CSR cycle.

The described basic operation of the detection and therapy delivery processes of this embodiment can be supplemented by additional control loops to make any stimulation device or other therapy delivery device more practical. For example, software can analyze 207 the respiratory waveform acquired and stored in the device memory for breathing parameters such as respiratory rate, tidal volume, cyclic changes of tidal volume (crescendo-decrescendo), and periodicity of respiration. Based on these parameters the software can determine the settings for the stimulation generator 205. For example, the duration of the stimulation train 208 can be determined based on the respiratory rate or on the success of the previous cycles of therapy. The stimulation duration can be automatically set to some number between, for example, 0.5 and 60 seconds, thus determining how long the respiratory drive will be suppressed. Based on the available data from the analysis of stored waveforms, the software can also turn therapy on and off 209 or decide to extend one breath or a number of breaths. In one illustrative embodiment stimulation is applied for the duration of a hyperpnea cycle.

In a further embodiment the software can calculate the respiratory effort breath-to-breath 210 based, for example, on the detected chest motion 203. Software can adjust stimulation energy 211 by changing, for example, settings for pulse current, signal duration or pulse frequency depending of the detected breath pattern. As used herein, the terms "stimulation signal," "stimulation," "stimulation pulse train," and equivalents refer to a single pulse or a train of pulses that operatively act as a single stimulation event.

In one embodiment in accordance with the invention, one hemidiaphragm of the patient is stimulated and remains in a relatively contracted state while the other can be naturally relaxed. This results in the trapping of a certain amount of air in the stimulated lung, which may even remain substantially inflated during stimulation. The level of stimulation may be chosen to keep the lung sufficiently inflated so that the stretch receptors in the lung act to activate the afferent vagal feedback to the patient's natural respiration control center in the autonomic nervous system. This feedback may suppress the patient's natural drive to breathe during the stimulation, and for a short time after the stimulation is ended, until both lungs are fully deflated. When the term "stimulated lung" is mentioned, it refers to the lung associated with a stimulated hemidiaphragm or the lung associated with a stimulated phrenic nerve. The term "stimulated lung" is used to simplify the description, and the stimulation of the corresponding hemidiaphragm or phrenic nerve is implied. "Unstimulated lung" can refer to an instance where no stimulation is applied or to a lung that is contralateral to a stimulated lung. It is understood that unless otherwise specified, both the right and left hemidiaphragms and/or phrenic nerves may be stimulated separately and independently, in combination, or in alternating patterns.

Whether or not the stimulation energy is sufficient to activate this vagal afferent feedback, the stimulated breath is extended. The breathing rate and minute ventilation are momentarily reduced. This results in the reduction of respiratory overshoot and consequentially may prevent blood $PaCO_2$ (Arterial blood carbon dioxide concentration) from dropping below an apnic threshold. As a result, the apnic phase of the CSR cycle may be prevented or substantially reduced in duration and/or severity.

Software can identify the cyclic breathing or CSR that is a periodic alternation of apnea-hypopnea and hyperpnea phases that together form a CSR cycle. Within the cycle software can identify apnea-hypopnea that is a cessation of breathing for several breaths or several sequential breaths of very week breathing. Software can identify the onset of hyperpnea that is a sequence of breaths with sequentially increasing tidal volume following apnea-hypopnea. Software can extend one or several breaths in the beginning or middle of hyperpnea phase of the cycle. Software can analyze the stimulated breaths for the effects of stimulation. These effects can include the additional inhaled volume, duration and presence of a plateau and the increased stimulated breath duration. Software can compare the results of stimulation to the desired settings, to the unstimulated breaths of the same patient and the previous stimulated breaths of the same patient that are stored in the device memory.

The general purpose of the feedback control is to achieve the desired extension of the breath at the minimum expanding of stimulation energy and with a minimum additional inspired tidal volume that can result from stimulation and additional diaphragmic contraction. Closed loop control algorithms such as PID controllers can be used to meter the adjustments based on the real time information and the process history.

Figure 3:
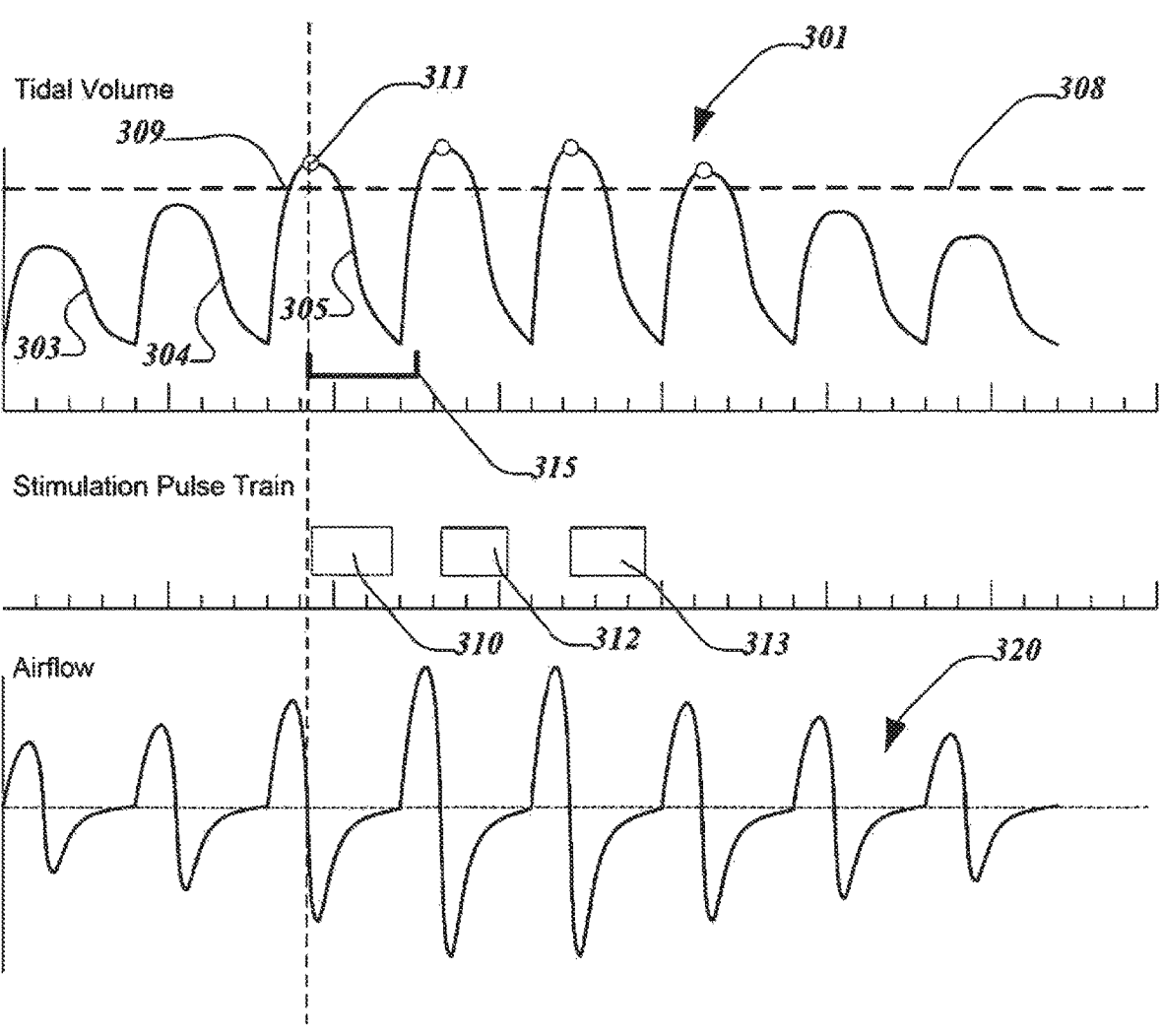
FIG. 3 is a stylized representation of tidal volume, airflow, and an illustrative stimulation therapy.

FIG. 3 is a stylized representation of tidal volume, airflow, and an illustrative stimulation therapy in accordance with embodiments of the invention. Tidal volume waveform 301 and airflow waveform 320 are shown during hyperpnea. Breaths 303, 304 and 305 sequentially increase in amplitude by increments of tidal volume that exceed 20% of the preceding breath. They therefore meet the criteria for stimulation set by an illustrative software algorithm for the detection of hyperpnea. In addition a tidal volume threshold criterion may set as illustrated by the by the line 308. In some embodiments, the stimulation pulse train 310 is activated only if the breath tidal volume 309 exceeds the threshold 308.

In this embodiment, stimulation is applied at the peak inspiration time point 311 when the breath phases change from inspiration to expiration. In this example three stimulation pulse trains 310, 312 and 313 are applied to three sequential breaths. In similar embodiments, stimulation may be applied at any point during inspiration. In those embodiments where the stimulation is applied at different points of inspiration, it may be helpful to fashion the stimulation pulse train so that the stimulation is applied somewhat gradually to move the diaphragm to a contracted position more gently to avoid arousing a sleeping patient.

In some embodiments, an additional stimulation criterion may be set by a blanking period 315. Blanking period can be set, for example, equal to the duration of time that is between 25% and 90% of the duration of an average spontaneous (unstimulated) breath for the treated patient or to some fixed value such as, for example, one second. The blanking period is applied to avoid double triggering. During the blanking period 315, stimulation is not allowed even if all other criteria are met. The blanking period can be implemented as a software time counter that starts counting after a stimulation pulse train is applied. In embodiments where the stimulation is not coordinated with the peak of inspiration, the blanking period may be shorter, particularly if the stimulation is configured to hold the lung "still" for a relatively long time.

Figure 4:
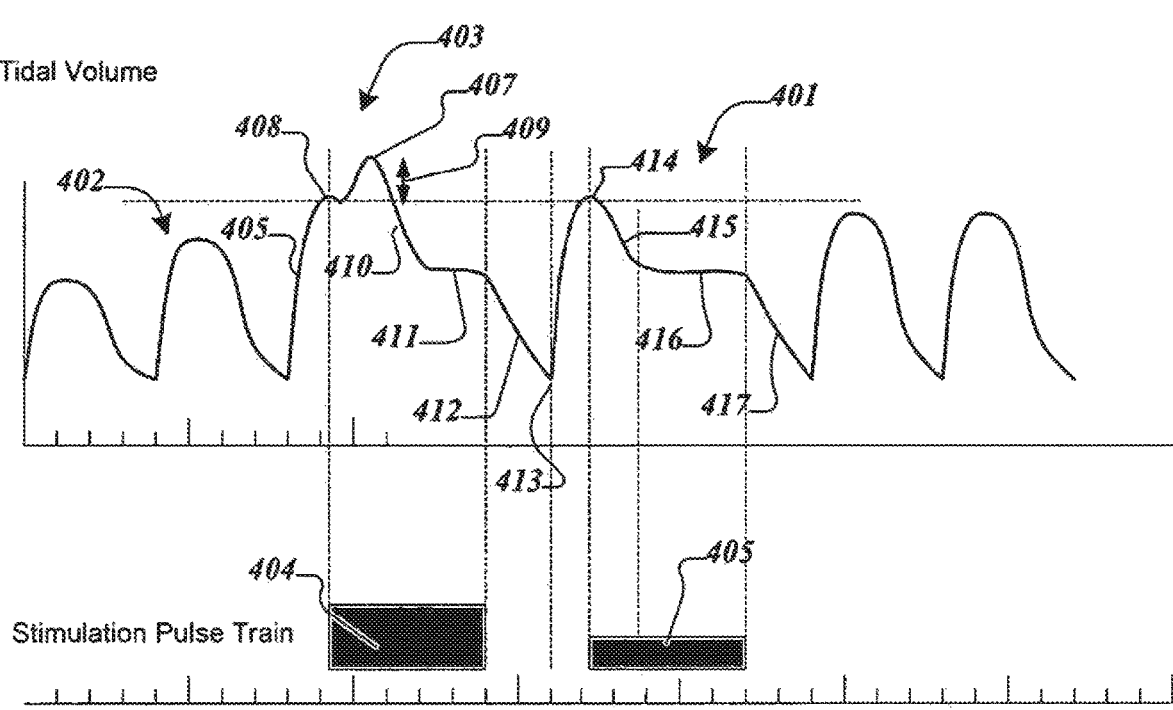
FIG. 4 is a stylized representation of a stimulation protocol.

FIG. 4 is a stylized representation of a stimulation protocol in accordance with embodiments of the invention. In this embodiment, an adjustment is made based on the results of the stimulation of the previous breath, but it is understood that such an adjustment can be performed based on the acquired respiratory data collected over several stimulated breaths or within the same breath.

FIG. 4 shows a representation of a respiratory waveform during a hyperpnea cycle. Breath 402 is not stimulated. Breath 403 is the first stimulated breath of the cycle. Stimulation pulse train 404 is applied shortly after the natural inspiration phase 405 of the breath 403 has reached the natural peak inspiration point 408. In this case the stimulation energy of the pulse train 404 may be excessive. Natural inspiration 405 is followed by the additional inspiration 407 caused by the stimulation and that results in the added tidal volume 409. Simultaneously with the stimulated lung inspiring the additional volume 409, the contralateral unstimulated lung starts expiring air 410. This is the first of two expirations that have been seen during the unilateral (single lung) stimulation performed according to embodiments of the invention. In this example, first lung expiration 410 stops when approximately 50% of air inhaled by the patient during the inspiration phase 405 is exhaled and the patient's lungs enter into a plateau or still period 411. This still period 411 can be shortened or prolonged by decreasing or increasing the duration of the stimulation pulse train 404. When stimulation 404 stops, the second (stimulated) lung enters the second expiration phase of the stimulated breath cycle 412 that ends at the point when both lungs are substantially deflated 413. It is believed that the stimulated lung's stretch receptor feedback inhibits the next breath, which can be started by the autonomic control system after expiration is completed.

Breath 401 is stimulated by the pulse train 405. The stimulation energy of the pulse train 405 is reduced compared to the pulse train 404 based on the analysis of the breath 403. Reduction can be achieved by reducing the electric current of pulse train, the duration of pulse train or the frequency of stimulation. The reduction of energy has the effect on the shape of the breath 401 compared to the breath 403. Stimulation 405 starts at the peak of natural inspiration 414 and there is no significant additional inspiration or added tidal volume caused by the stimulation. Expiration of the unstimulated lung 415 is followed by a plateau 416 that is followed by the expiration of the stimulated lung 417. It is understood that the optimization of the stimulation energy can be performed in small increments from one stimulated breath to another and involve feedback mechanisms such as a digital PI or PID regulators and other tools commonly used by engineers to design feedback loops and controls.

In some embodiments, the stimulation energy is allowed or designed to add tidal volume to an intrinsic breath. This is of course true where the breath is a diminished or apnea-hypopnea breath, but it also may be the case that some therapies are designed or allowed to add tidal volume to intrinsic breaths during normal respiration or hyperpnea (particularly near the start or end of the hyperpnea phase). In these cases calibration of the stimulation signal may be based on factors other than a desire to minimize additional inspiration caused by stimulation.

Figure 5:
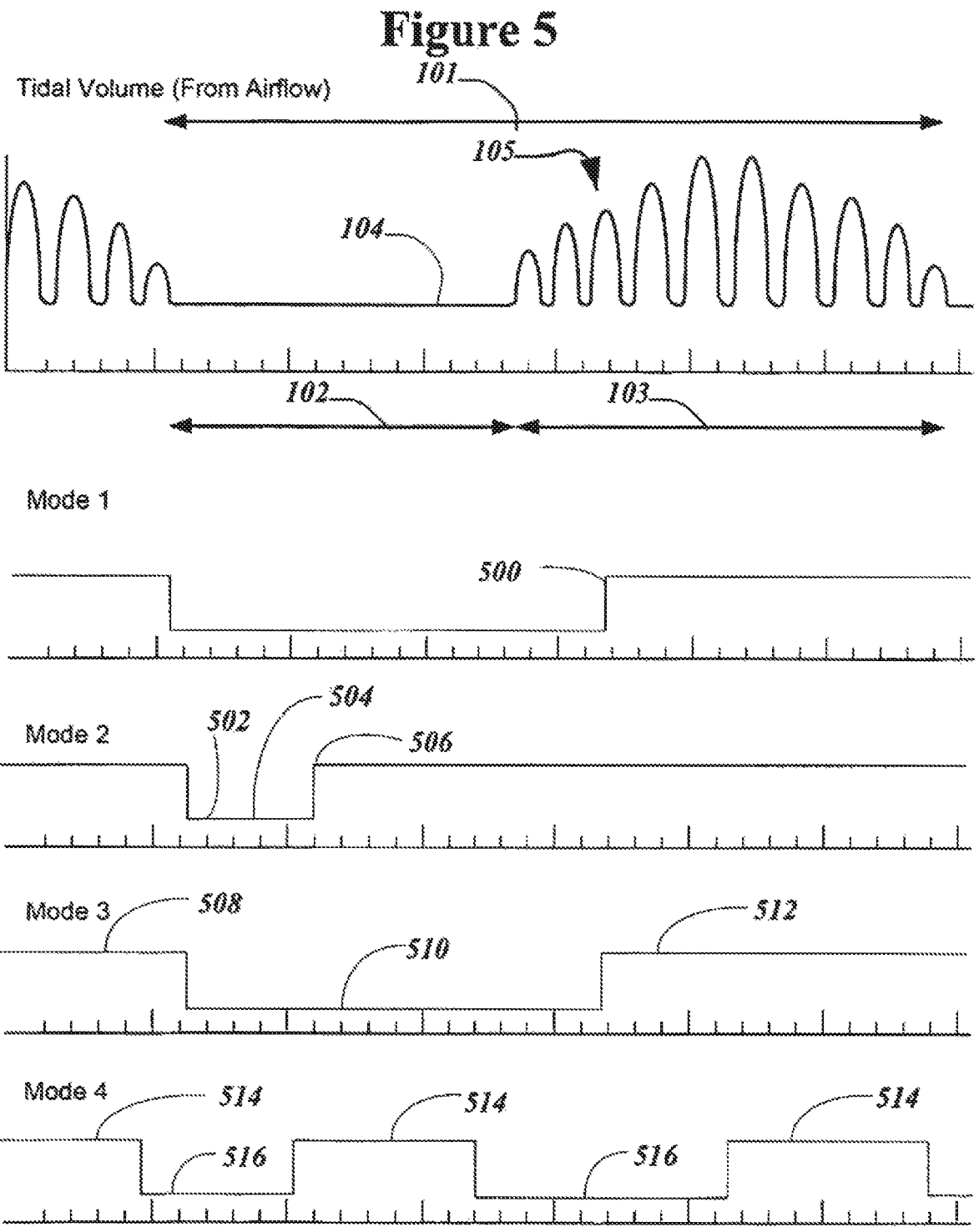
FIG. 5 is a stylized representation of tidal volume during a CSR cycle with mixed apnea and several treatment protocols.

FIG. 5 is a stylized representation of tidal volume during a CSR cycle with mixed apnea and several treatment protocols in accordance with embodiments of the invention. The CSR cycle is the same as is shown and described with respect to FIG. 1. The various treatment protocols, or modes, are shown in a simplified fashion below the representation of the CSR cycle. The effects of the stimulation profile on the tidal volume are not shown in this Figure, but will be discussed here and elsewhere. Mode 1 is a stimulation that begins 500 upon the detection of hyperpnea and continues through the majority of the hyperpnea cycle. It is believed that holding at least one lung still during the hyperpnea cycle reduces respiration during that cycle and thus reduces the likelihood of ventilatory overshoot and a subsequent reduced breathing period that could result from such an overshoot.

Mode 2 is a stimulate and hold mode similar to mode 1. In mode 2, apnea-hypopnea is detected at 502. After a delay of an adjustable set amount 504, a stimulation pulse train is initiated 506 and held through the majority of the hyperpnea cycle. As with any of the modes, the stimulation may be shaped to gradually capture and contract the diaphragm so as to be less likely to arouse the patient or cause discomfort.

Mode 3 stimulates and holds at least one hemidiaphragm based on a historical average duration of hyperpnea and apnea-hypopnea cycles. If a patient has not immediately responded to therapy, mode 3 would stimulate and hold based on historical durations of apnea-hypopnea 510 and hyperpnea 512. The stimulation 512 and blanking period 510 would be based on these average durations and not on any real-time detection of breathing parameters. This mode might be useful if a patient's movement during sleep makes it difficult to measure respiration parameters accurately, for example.

Mode 4 stimulates and holds at least one hemidiaphragm for random periods 514 at random intervals 516. This mode may be effective because holding at least one lung still during apnea-hypopnea has little effect, while desirable effects flow from holding one lung still during periods of hypopnea. This mode may be effective for some patients and is very simple to implement and manage. This mode may be automatically triggered upon detection of sleep by the use of an accelerometer and/or position sensor or any other means known in the art. Sleep detection may be used to trigger or terminate or otherwise manage any of these modes.

Figure 6:
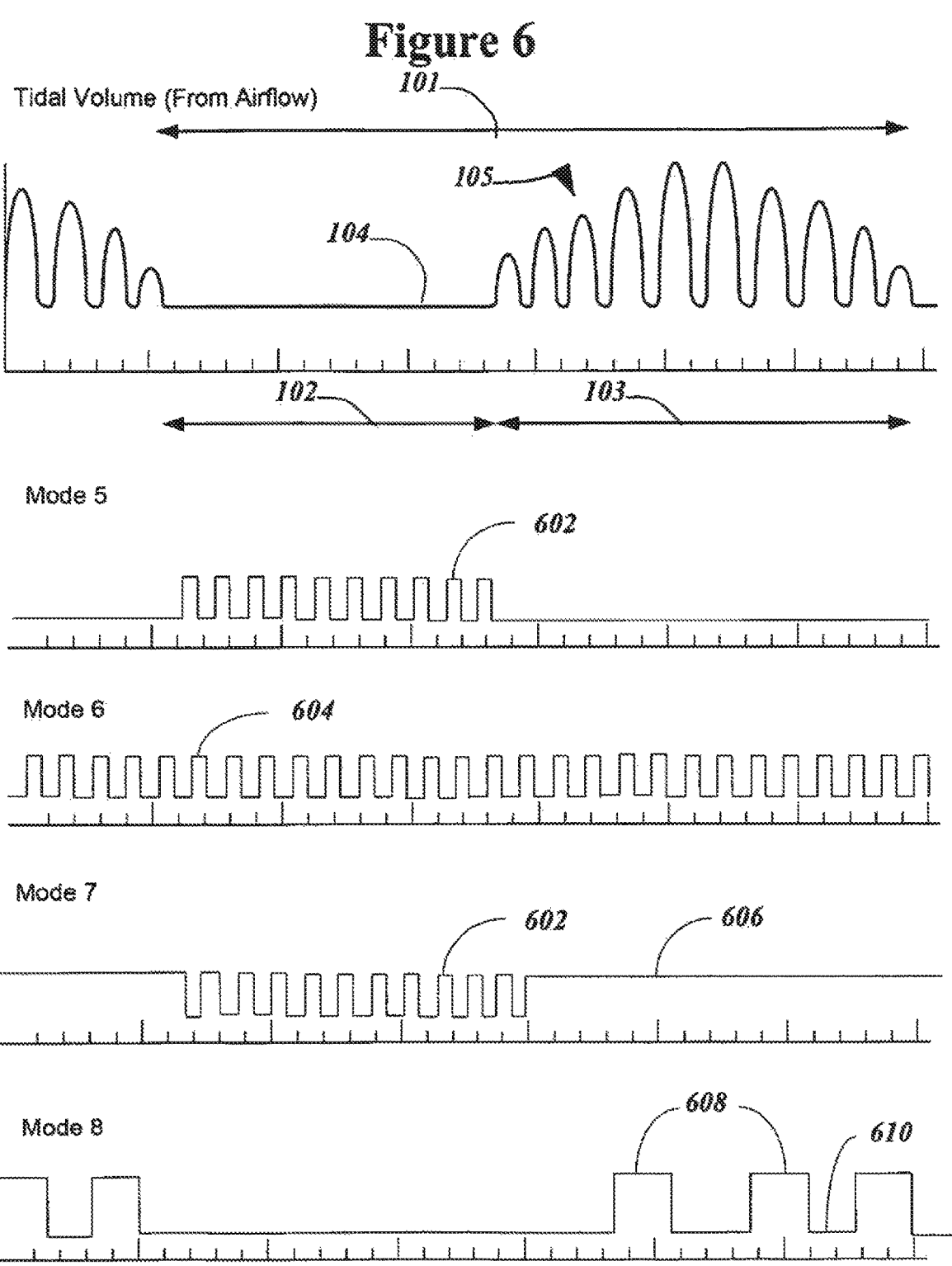
FIG. 6 is a stylized representation of tidal volume during a CSR cycle with mixed apnea and several treatment protocols.

FIG. 6 is a stylized representation of tidal volume during a CSR cycle with mixed apnea and several treatment protocols in accordance with embodiments of the invention. The CSR cycle is the same as is shown and described with respect to FIG. 1. The various treatment protocols, or modes, are shown in a simplified fashion below the representation of the CSR cycle. The effects of the stimulation profile on the tidal volume are not shown in this Figure, but will be discussed here and elsewhere. Mode 5 comprises a series of short stimulation signals 602 during apnea-hypopnea. This mode could be employed by detecting actual apnea-hypopnea episodes and stimulating for the majority of the duration of the reduced autonomic breathing. The short pulses of mode 5 are designed to stimulate respiration during the apnea-hypopnea phase where less than normal respiratory drive is present. Each signal is intended to create or augment a breath.

When employing mode 5, it may be important not to contribute to the hyperventilation or excessive ventilation. Mode 5 will therefore often be configured to stimulate breathing at below mean ventilation levels. One possible way of accomplishing this would be to stimulate one lung at a time. The stimulation could also be set to send the stimulation signals at 50% of normal breathing rate, 50% of the apnea hyperpnea periodic breathing cycle, or some arbitrary low number such as 6-10 breaths per minute or it could be set to stimulate for 50% of the apnea-hypopnea duration, for example. The stimulation of mode 5 during apnea-hypopnea may reduce oxygen desaturation which may reduce respiratory overshoot by keeping the blood gases at a more consistent level.

Patients with mixed apnea may also differ in the degree of airway obstruction (obstructive component of apnea). In general, the airway diameter may fluctuate with the CSR cycle. The airway may be more open during hyperpnea and gradually more closed during a decrescendo of hyperpnea and apnea-hypopnea. In many cases, significant airway closure is observed towards the end of apnea-hypopnea. This can contribute to arousals at the beginning of hyperpnea, when the patient starts breathing against the closed or significantly obstructed airway. In this regard it may be advisable in some cases to engage the stimulation of mode 5 in the early stages of apnea-hypopnea when airway closure may be less likely.

Mode 6 comprises a series of short stimulation bursts 604 throughout the CSR cycle. It has been observed that in some patients stimulating throughout CSR without regard to synchronizing the stimulations to breathing or any phase of breathing may "train" the poorly functioning autonomic control to engage in more regular control of breathing. The stimulation signal in mode 6 may be on the order of one to two seconds.

It has been observed that the crescendo-decrescendo pattern of a typical hyperpnea cycle may represent a relatively strong respiratory drive early in the hyperpnea cycle that gradually decreases during the decrescendo phase of the hyperpnea. It is believed that initiating a mode 6 stimulation pattern after the midpoint of the hyperpnea cycle may be effective in maintaining a regular breathing pattern for the duration of the stimulation and may actually result in regular autonomic breathing once the stimulation is terminated.

Mode 7 comprises a series of short stimulation bursts 602 during apnea-hypopnea with an extended stimulation and hold during hyperpnea 606. It has been observed that the drive to hyperventilate in CSR patients may vary throughout the night. For example, it may be most severe early in the sleep cycle and may wane some as the patient falls more deeply into sleep or as therapies mitigate the drive. It may be advisable in some cases to implement mode 7 early in a sleep period and then move to mode 1 or another mode as the therapy mitigates the disordered breathing.

The reverse may also be true, as the ultimate goal is to stabilize breathing. A patient therapy may be started on mode 1 with the hope that attenuating respiration during hyperpnea will reduce respiratory overshoot and result in autonomic breathing replacing apnea-hypopnea. If mode 1 is not effective in breaking the CSR cycle after some time, the device could switch to mode 7 or some other mode to provide some ventilation during apnea-hypopnea cycles and reduce blood oxygen desaturation incidents.

Mode 8 comprises a number of longer segmented signals 608 during hyperpnea. The signals are separated by intervals 610 so that the signals hold at least one hemidiaphragm still during hyperpnea for several discontinuous periods.

All of the modes just described, and others that will occur to those of skill in the art upon reading this disclosure, may be combined into a single therapy delivery device. These modes may be selected based on a patient's response to therapy and other factors considered by practitioners that treat disordered breathing.

Figure 7:
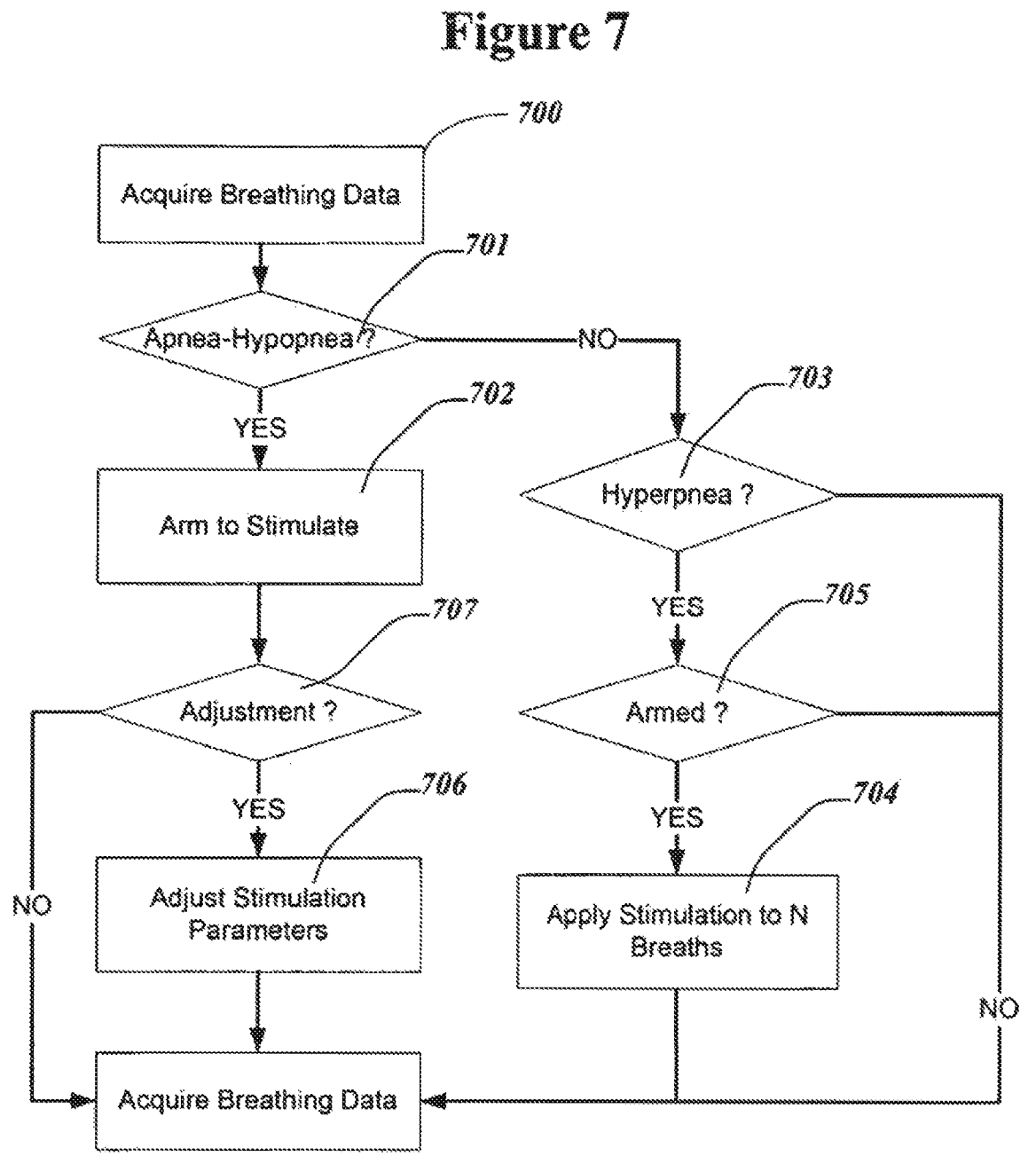

FIG. 7 is a flowchart of a detection and treatment protocol in accordance with embodiments of the invention. Respiratory data of a patient is gathered 700 from sensors capable of detecting signals representative of respiration frequency and amplitude. The data is then analyzed 701 to determine if the patient is experiencing an episode that can be characterized as apnea-hypopnea. Clinically, apnea is defined as 10 seconds or more of very little (less than 10% of normal for the patient) breathing or no breathing at all. For practical purposes apnea-hypopnea can be detected as 4-9 seconds without breathing or with very shallow breathing. Very shallow breathing can be defined as, for example, less than 5-20% of highest tidal volume previously detected during the previous CSR cycle or over selected several minutes of spontaneous ventilation or as less than 10% of patient's normal, non-periodic breathing. The thresholds for apnea-hypopnea detection can be automatically periodically adjusted based on the respiratory information stored in the device memory or adjusted by a practitioner based on characteristics of the individual patient.

If apnea-hypopnea is detected, it can be used to enable therapy during a following hyperpnea cycle. The stimulation device may be "armed" 702 upon detection of apnea-hypopnea and would be set to intervene and moderate respiratory overshoot upon the onset of hyperpnea. Intervention can occur within the same CSR cycle or during one of the following cycles.

In one embodiment the protocol will detect apnea-hypopnea, wait for the first breath that meets the hyperpnea criteria 703, and start stimulation as soon as the first breath occurs following apnea-hypopnea. In this embodiment, the hyperpnea criteria may be a simple amplitude threshold that is normally crossed as the patient moves from apnea-hypopnea to hyperpnea.

Another embodiment assumes a relatively long stimulation duration of 30-60 seconds. In this embodiment hyperpnea is suppressed, as in others, and stimulation may or may not be synchronized to inspiration-expiration.

In another embodiment, the device detects hyperpnea 703 by analyzing the respiratory waveform over several breaths. Hyperpnea can be detected 703, for example, by three sequential breaths where the tidal volume of the next breath exceeds the tidal volume of the previous breath by 20% or more. If such sequentially escalating breaths are detected, a device may apply stimulation to the following breath or several breaths 704 if armed 705. It can be expected that the device will intervene and extend at least one breath after, for example, the first 4-10 breathes of hyperpnea are detected and analyzed. Other methods of detecting or declaring hyperpnea may be used without departing from the spirit of this disclosure. Some patients may have hyperpneas that do not follow the crescendo-decrescendo pattern that is frequently found in CSR, and hyperpnea detection criteria can be set on a case-by-case basis.

The protocol may decide 707 to adjust the parameters of stimulation 706 based on the data collected 700 from the intervention (the physiologic response to stimulation) during one or more previous CSR cycles. These parameters can include: stimulation duration, stimulation energy and the number of extended breaths.

Figure 8:
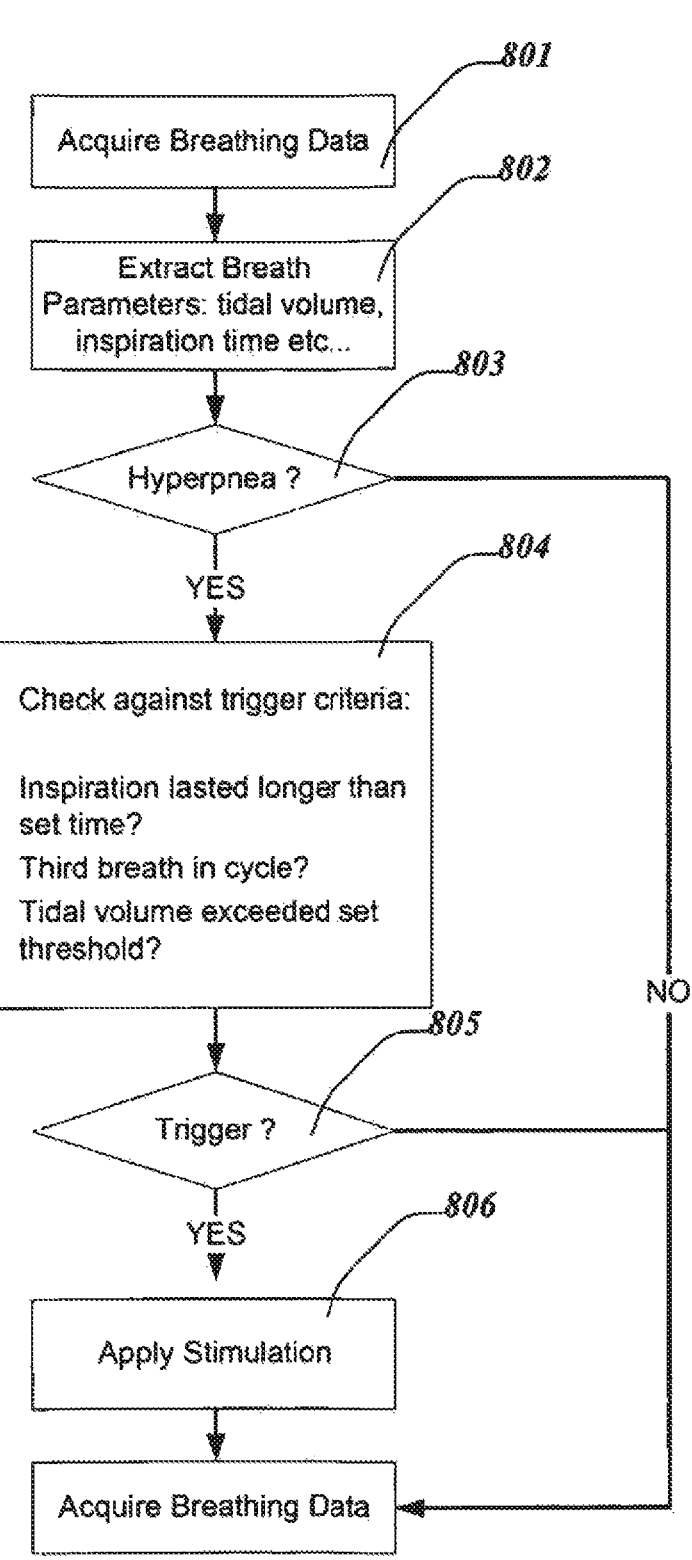
FIG. 8 is a flowchart of a detection and treatment protocol.

FIG. 8 is a flowchart of a detection and treatment protocol in accordance with embodiments of the invention. This protocol can be executed alone or in combination with other protocols. For example, this protocol could be executed within the block 704 in FIG. 7. It could represent the decisions made within one breath after the hyperpnea is identified in block 703 of FIG. 7. In the event that this protocol is nested within the protocol of FIG. 7, the redundant steps (i.e., hyperpnea detection) would not be performed.

In the embodiment of FIG. 8 as a stand-alone protocol, respiratory waveform data is acquired 801 from a respiration sensor in real time, for example every 10 milliseconds. The detected beginning of the inspiration phase of the breath starts the breath analysis 802. As the data points are acquired, a value representative of inspired tidal volume gradually increases. If hyperpnea is not detected 803, further respiratory waveform data is gathered 801. If hyperpnea is detected, parameters such as tidal volume at the end of inspiration, inspiration duration and the rate of inspiration (volume divided by time) are calculated and analyzed 804.

The protocol may decide 805 to trigger or not trigger the application of a stimulation pulse train or even to abort the pulse train before the normal duration time based on this constantly updated data stream and analysis. The breath analysis 804 may include, without limitations, the following tests:

If the inspiration duration is less than a preset time of, for example, 0.5 sec. or is less than 75% of the inspiration time of an average breath for this patient, or some predetermined fraction of the inspiration time of the previous breath, stimulation may not be triggered. Conversely if the inspiration duration is significantly longer than expected, stimulation also may not be triggered.

Figures 9, 10:
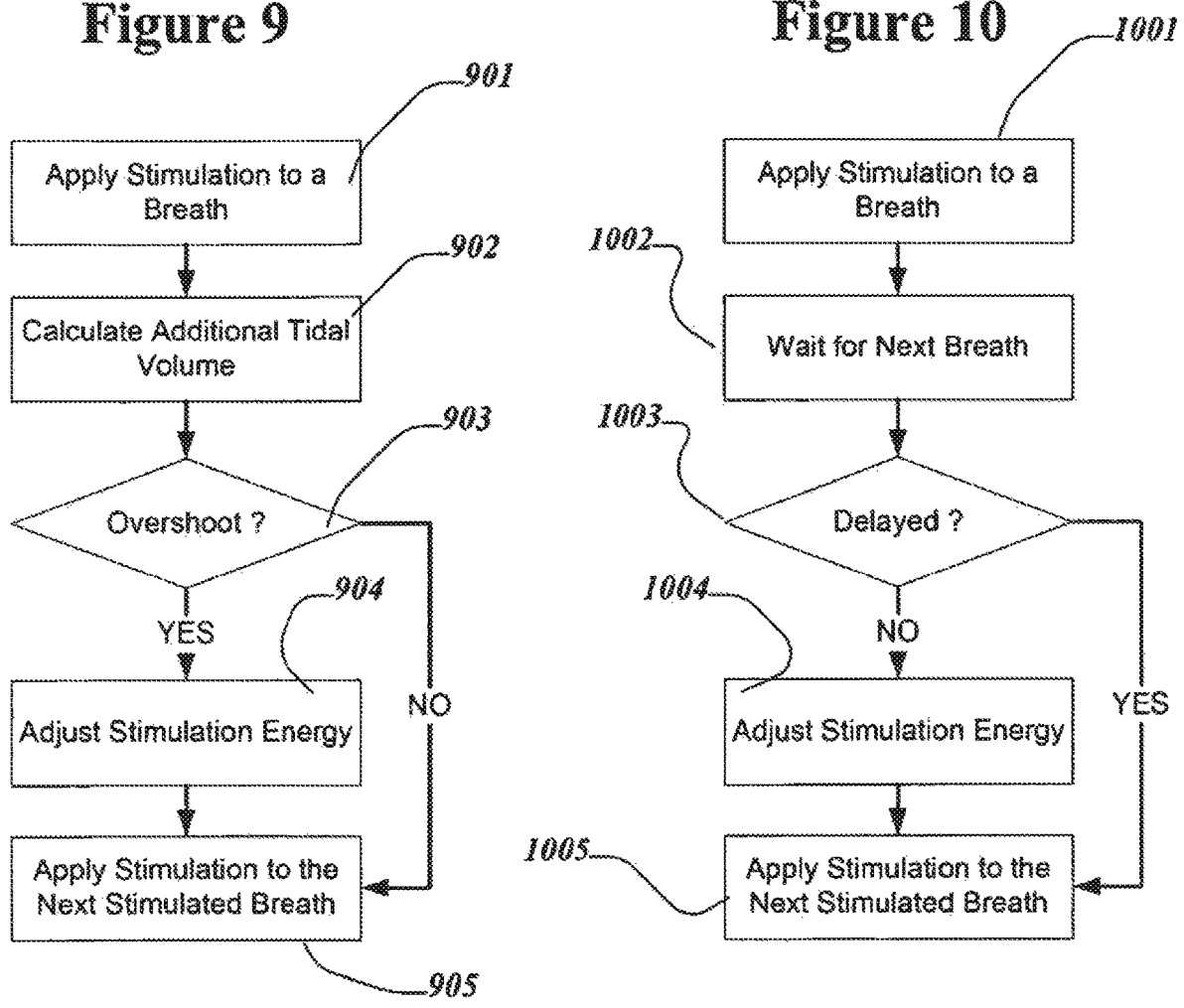
FIG. 9 is a flowchart of a stimulation adjustment protocol.
FIG. 10 is a flowchart of a stimulation adjustment protocol.

FIG. 9 is a flowchart of a stimulation adjustment protocol in accordance with embodiments of the invention. The protocol of FIG. 9 may be used to accomplish the signal adjustment described in relation to FIG. 4. After the stimulated breath 901 is substantially completed, the additional tidal volume as compared to an unstimulated breath is calculated 902. If an overstimulation is detected 903, such as for example an additional 10% of tidal volume is inhaled by the patient after the natural peak of inspiration is reached, the energy of stimulation is adjusted 904 before the stimulation of the next stimulated breath 905. The adjustment may constitute a 10% reduction of the stimulation current or signal duration.

FIG. 10 is a flowchart of a stimulation adjustment protocol in accordance with embodiments of the invention. It is possible that, the adjustment of energy illustrated by FIG. 9 can result in the loss of respiratory inhibition or, in the case of nerve stimulation, the loss of nerve capture. This loss of inhibition can be detected by the absence of the stimulated breath plateau (See FIG. 4 and related discussion) in response to the application of stimulation 1001 or by the increase of respiratory rate indicated by the absence of the expected delay 1002 before the next breath 1003. If the breath is not delayed or the plateau is not detected, the stimulation energy can be increased 1004 to be applied to the next stimulated breath 1005.

The general purpose of the feedback control is to achieve the desired contraction of the diaphragm with the minimum expanding of stimulation energy and with a minimum additional inspired tidal volume that can result from stimulation and additional diaphragmic contraction. Closed loop control systems such as PID controllers can be used to meter the adjustments based on the real time information and the process history.

An alternative method of determining if stimulation capturing the diaphragm is to apply a short stimulation signal during apnea-hypopnea. A short stimulation envelope, for example 2 seconds long, can be applied when no significant natural breathing occurs. The response to this stimulation can be measured as tidal volume or lung volume change. Such a capture test could be performed periodically and the energy of stimulation can be adjusted if indicated. Such test signals during apnea-hypopnea allow detection of stimulation capture with less interference from natural breathing.

Figure 11:
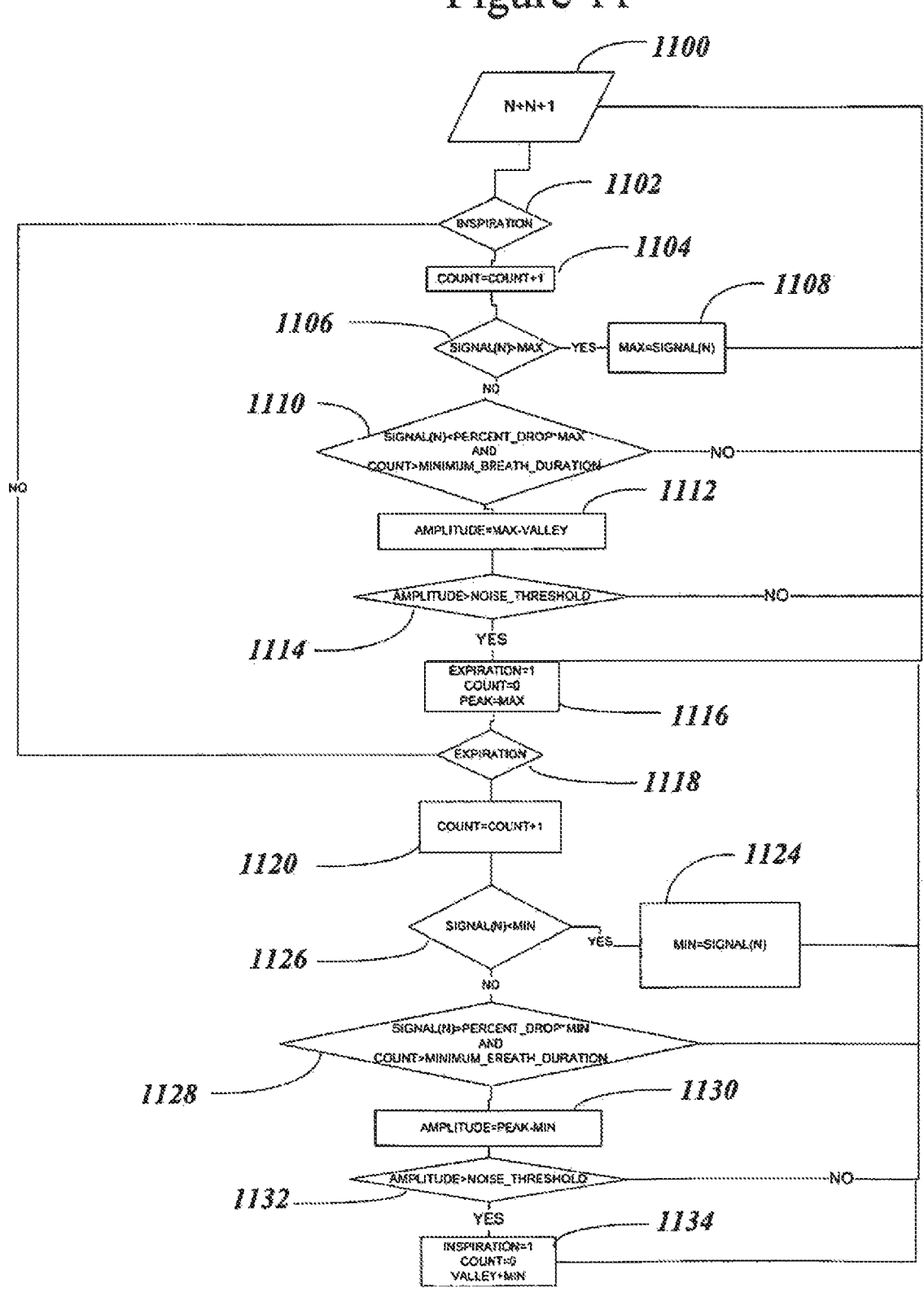
FIG. 11 is a flowchart of a breath detection protocol.

FIG. 11 is a flowchart of a breath detection protocol in accordance with embodiments of the invention. A signal (N)

is captured 1100 from a respiration sensor configured to sense respiratory effort of a patient. The sensor could be an impedance sensor, an accelerometer, an external respiration belt, or any other sensor known in the art. When the protocol is in the inspiration mode 1102, it counts the signal based on a sample frequency 1104. The protocol begins with a "MAX" value set at the system minimum and a "MIN" value set to the system maximum. The protocol originally assumes the patient is in inspiration and compares the measured signal to the recorded MAX. If the signal is greater than MAX 1106, MAX is reset to the signal value 1108. This continues until the signal is less than MAX, at which time a noise detection protocol 1110 checks that the signal has not dropped an unreasonable amount, which might indicate a signal interruption or noise, and that the count since the beginning of inspiration is greater than a preset or calculated minimum breath duration. If the detected peak of inspiration indicated by the decreasing signal is determined to be real, an amplitude representative of tidal volume is calculated 1112 by subtracting the new MAX from the most recently determined VALLEY (discussed below). If this amplitude passes a noise threshold 1114 the expiration loop is initiated 1116 and a PEAK value is assigned the value of MAX, or the most recent signal.

The expiration loop 1118 begins with a counter 1120 that accumulates signal data during the expiration cycle. If the signal is less than MIN 1126, MIN is reset to the signal value 1124. This continues until the signal is greater than MIN, at which time a noise detection protocol 1128 checks that the signal is not unreasonably greater than MIN and that the count since the beginning of expiration is greater than a preset or calculated minimum breath duration. If the detected valley of expiration indicated by the now-increasing signal is determined to be real, an amplitude representative of tidal volume is calculated 1130 by subtracting the new MIN from the most recently determined PEAK. If this amplitude passes a noise threshold 1132, the inspiration loop is initiated 1134 and a VALLEY value is assigned to the value of MIN, or the most recent signal.

From this protocol, or others using the same basic framework or that will occur to those of skill in the art upon reading this disclosure, values for breath frequency or periodicity, amplitude or tidal volume, inspiration duration, expiration duration, cyclic changes of tidal volume, onset an peak of inspiration, onset and peak of expiration and others may be determined. Averages over time or over relevant periods of time may also be calculated. For example, a baseline breath duration may be calculated by measuring breath periodicity over a period of time and calculating an average value. Such baseline development may happen while a patient is awake or at other times when disordered breathing is less likely. Even during periods of CSR, average breath duration can be taken over several cycles of breathing and should remain reasonably constant and provide a good baseline.

Figure 12:
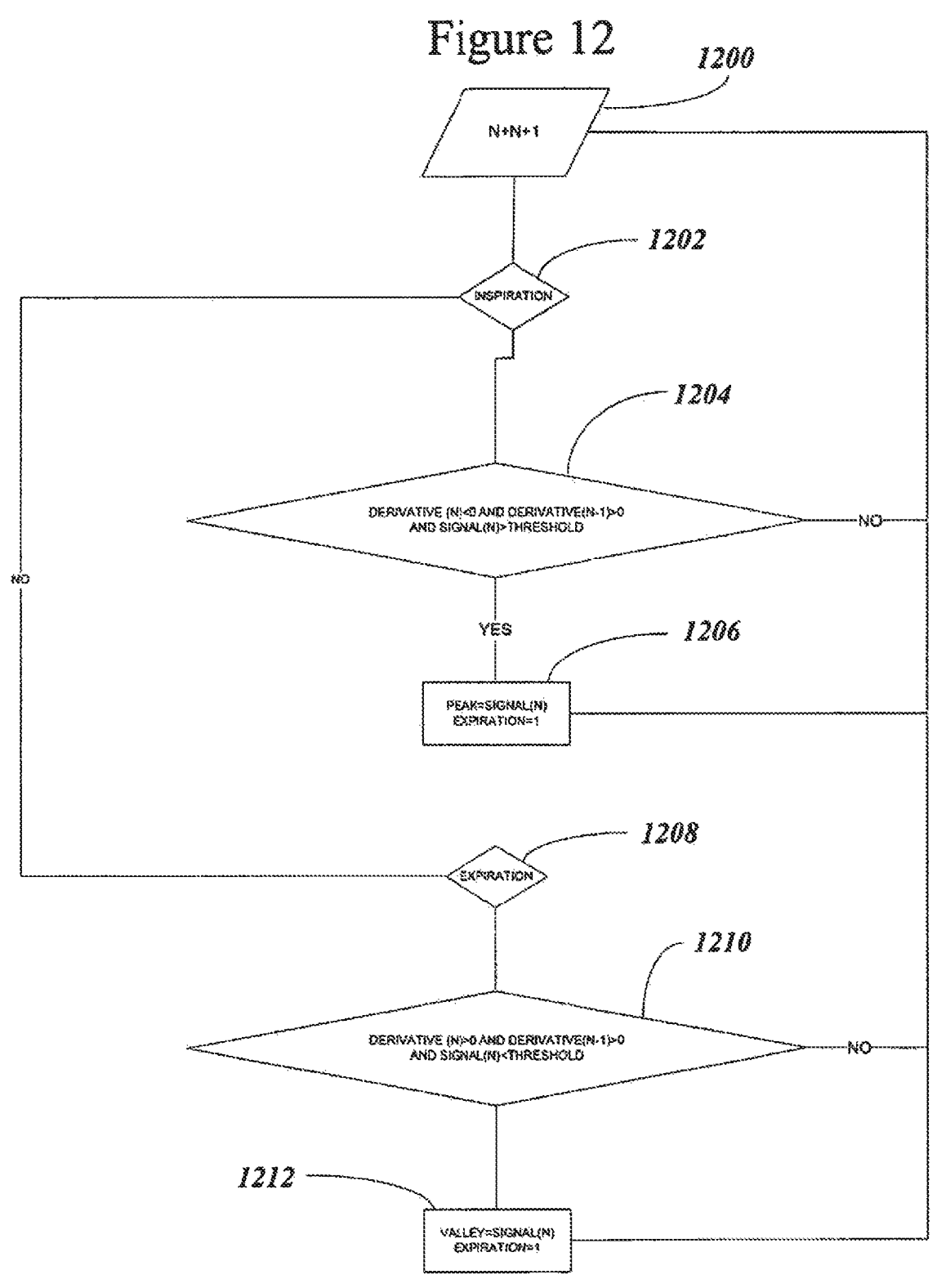
FIG. 12 is a flowchart of a breath detection protocol.

FIG. 12 is a flowchart of a breath detection protocol in accordance with embodiments of the invention. This protocol is another alternative method of determining cycles of inspiration and expiration and associated breathing data. A signal (N) is captured 1200 from a respiration sensor configured to sense respiratory effort of a patient. If the signal is processed through the inspiration loop 1202, the slope of the signal and the previous signal is determined and compared to zero 1204 to look for an inflection point. If the slope of the signals was positive and is now negative, and a noise threshold test is passed, it can be determined that a peak of inspiration has occurred. The peak value is recorded 1206 and the expiration module 1208 commences. The expiration module 1210 compares the slope of the data points, generally negative throughout expiration depending on the respiration sensor used, until the slope becomes positive. Once the slope of the signals changes from negative to positive, and a noise threshold test is passed, it can be determined that a valley of expiration has occurred and the valley can be recorded 1212 and the inspiration module can begin. This protocol can determine respiration qualities such as breath frequency or periodicity, amplitude or tidal volume, inspiration duration, expiration duration, cyclic changes of tidal volume, onset an peak of inspiration, onset and peak of expiration, for example.

Figure 13:
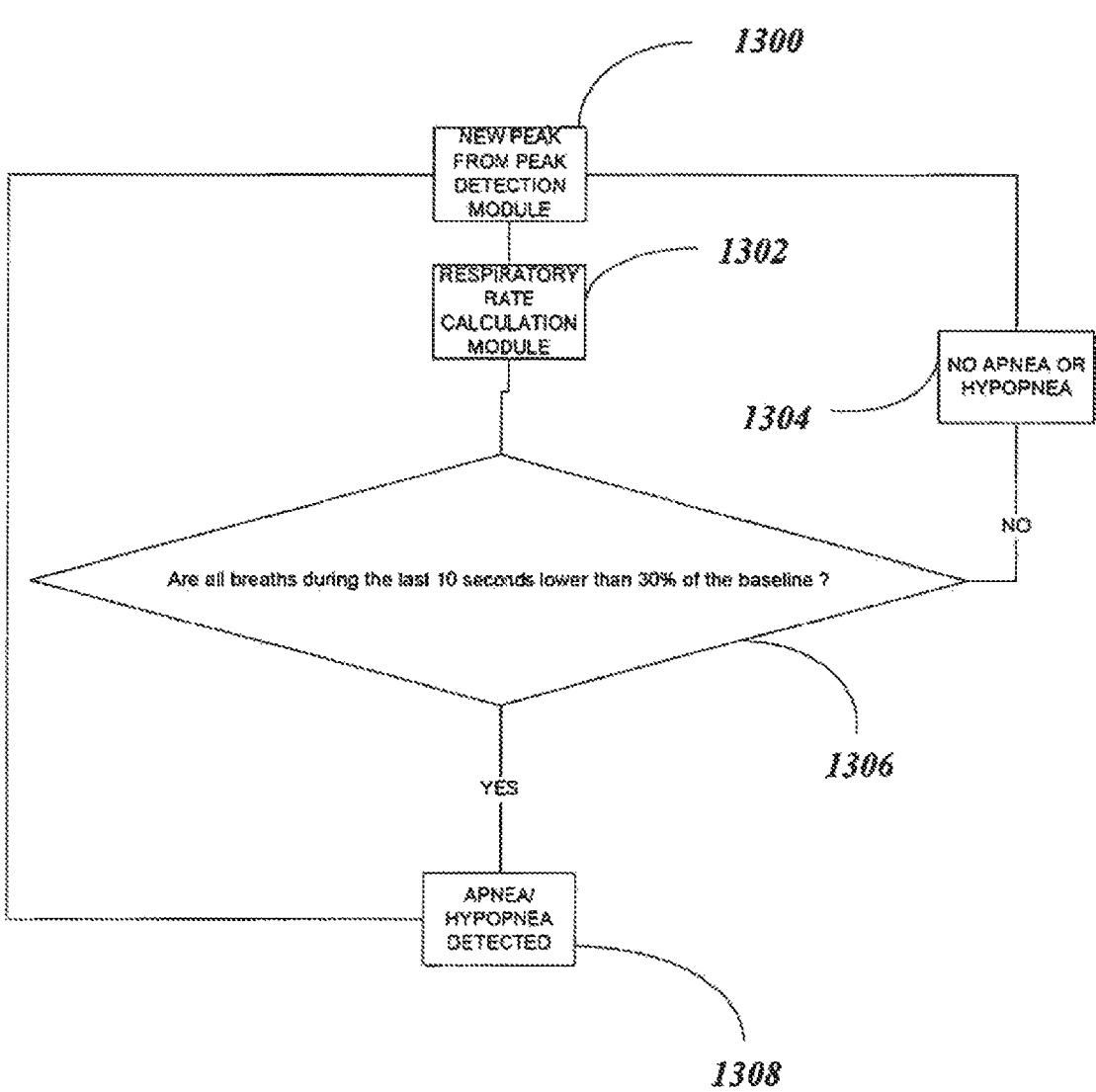
FIG. 13 is a flowchart of an apnea-hypopnea detection protocol.

FIG. 13 is a flowchart of an apnea-hypopnea detection protocol in accordance with embodiments of the invention. The protocol begins when a respiration peak is detected 1300 in accordance with a protocol such as those shown in FIGS. 11 and 12, or others. The respiration rate is then calculated 1302 based on accumulated data either in the peak detection module or this module. A baseline breath amplitude is determined 1306 for the patient. Such a baseline may be set based on breathing data collected during the day, in the case of a sleep apnea patient, or at any other time that regular breathing may be tracked. Alternatively, a baseline breath amplitude may be determined by a practitioner and preset into the protocol. However determined, the protocol checks to see whether all breaths in the last ten seconds lower than 30% of the baseline 1306. If so, apnea-hypopnea is detected. Other criteria could be used to detect and declare an episode of apnea-hypopnea, and all are contemplated within the scope of this disclosure.

Figure 14:
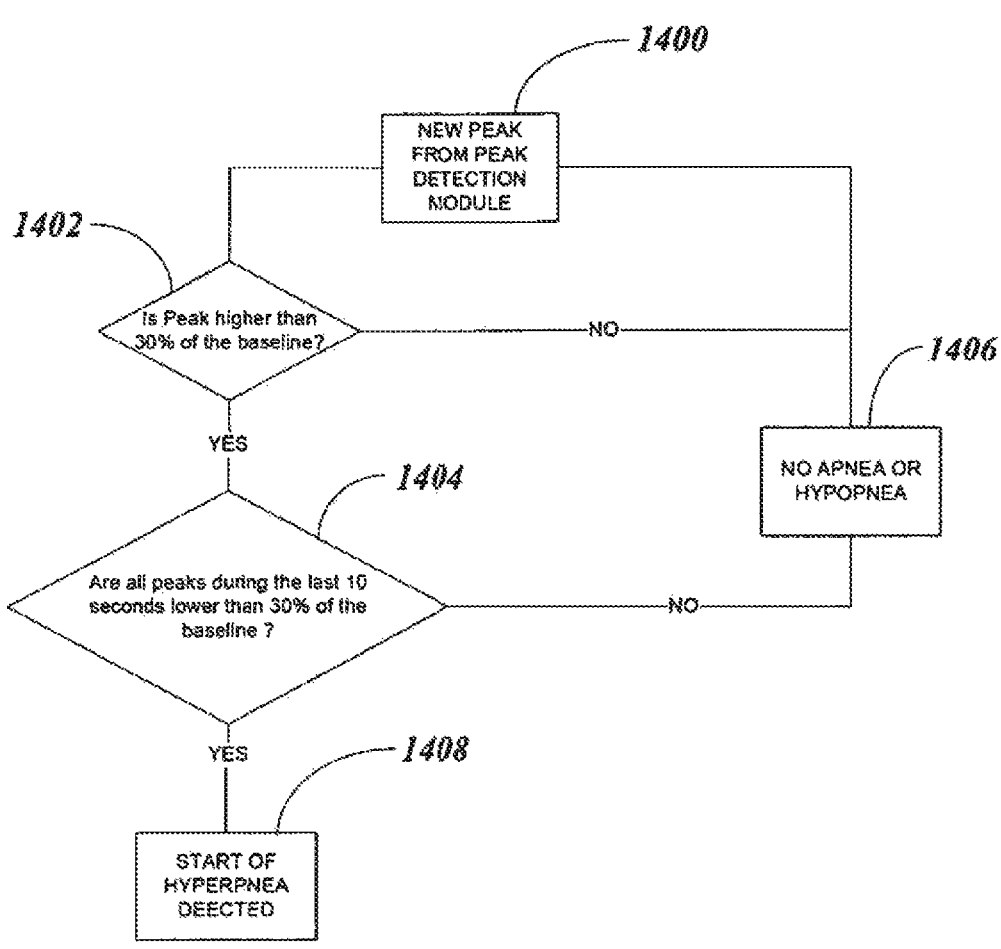
FIG. 14 is a flowchart of a hyperpnea detection protocol.

FIG. 14 is a flowchart of a hyperpnea detection protocol in accordance with embodiments of the invention. The protocol begins when a respiration peak is detected 1400 in accordance with a protocol such as those shown in FIGS. 11 and 12 or others. The protocol of FIG. 14 determines if the peak is higher than 30% of a baseline breath amplitude 1402 determined as described with respect to FIG. 13. If there is no such peak, the module waits for the next peak from the peak detection module 1400. Once the module detects a breath peak higher than 30% of the baseline 1402 it checks for a preceding apnea by determining if all peaks during the last 10 seconds were lower than 30% of baseline 1404. If both conditions 1402 and 1404 are met, the start of a hyperpnea cycle is detected 1408. The criteria for steps 1402 and 1404 may be modified as desired without departing from the spirit of this disclosure.

Figure 15:
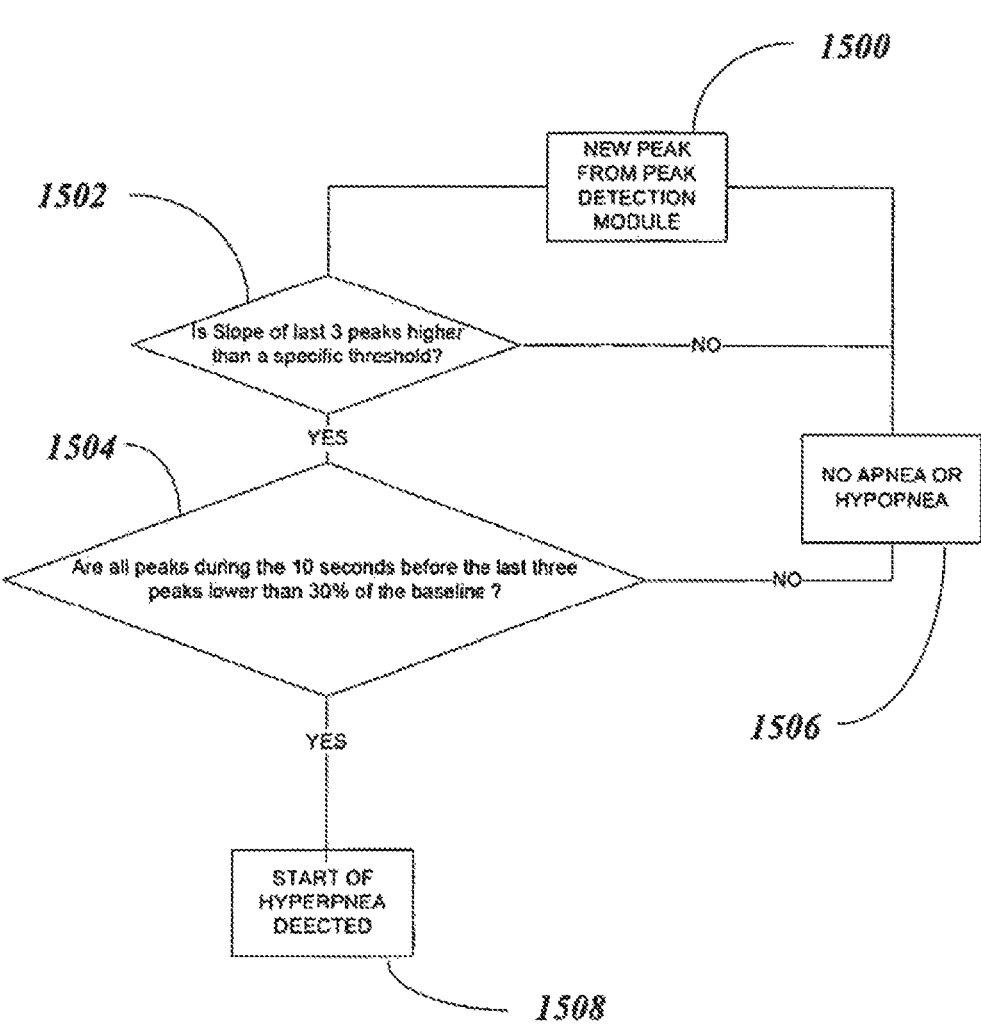
FIG. 15 is a flowchart of a hyperpnea detection protocol.

FIG. 15 is a flowchart of a hyperpnea detection protocol in accordance with embodiments of the invention. The protocol begins when a respiration peak is detected 1500 in accordance with a protocol such as those shown in FIGS. 11 and 12 or others. The protocol of FIG. 15 determines the slope of the last three detected peaks and compares the slope to a predetermined or historically determined threshold 1502. If the slope of the three peaks exceeds the threshold, the protocol determines whether all peaks recorded during the ten seconds prior to these three peaks had an amplitude lower than 30% of a baseline breath amplitude 1504. If both conditions 1502 and 1504 are met, the start of a hyperpnea cycle 1508 is detected. The criteria for steps 1402 and 1404 may be modified as desired without departing from the spirit of this disclosure.

Figure 16:
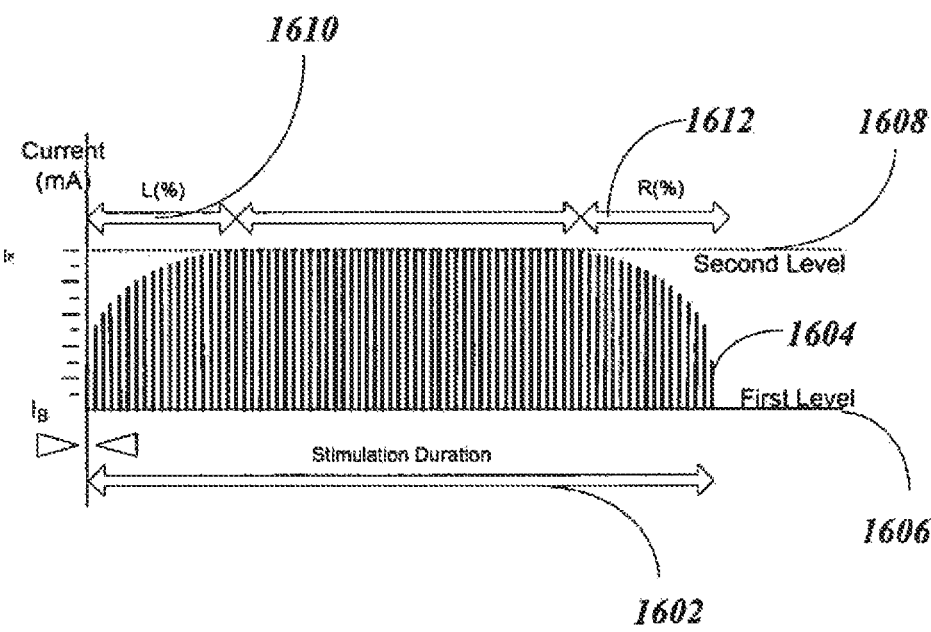
FIG. 16 is a representation of a stimulation signal.

FIG. 16 is a representation of a stimulation signal in accordance with embodiments of the invention. The stimulation signal lasts a stimulation duration or signal duration 1602. The stimulation signal is made up of a series of pulses 1604 represented by vertical lines in FIG. 16. In this example, when the stimulation is initiated, the current begins at a base or first level 1606. In some embodiments, the base current level 1606 is 1-2 milliamps (mA). The stimulation current amplitude then transitions 1610 over a percentage of the total duration to a plateau or second level 1608. In some embodiments, the plateau current level 1608 may be between 2-4 mA and the time to go from the base current level 1606 to the plateau is about 30% 1610 of the total signal duration 1602. The current amplitude may transition 1610 from the base current level to the plateau current level in a linear, exponential, or elliptical fashion or any other transition shape that may be useful. The gradual nature of this transition 1610 may help reduce patient discomfort and reduce or eliminate arousals during sleep. The current amplitude may also transition downward 1612 near the end of the stimulation signal in a similar fashion as the initial transition 1610. This may release the stimulation more gradually and may provide similar benefits for a patient.

The stimulation pulses 1604 in this example may be delivered at a frequency of 20 Hz and last for a period of 150 μsec. The stimulation duration or signal duration 1602 includes the entire time from that pulses are delivered including transition pulses 1610, 1612.

Figure 17:
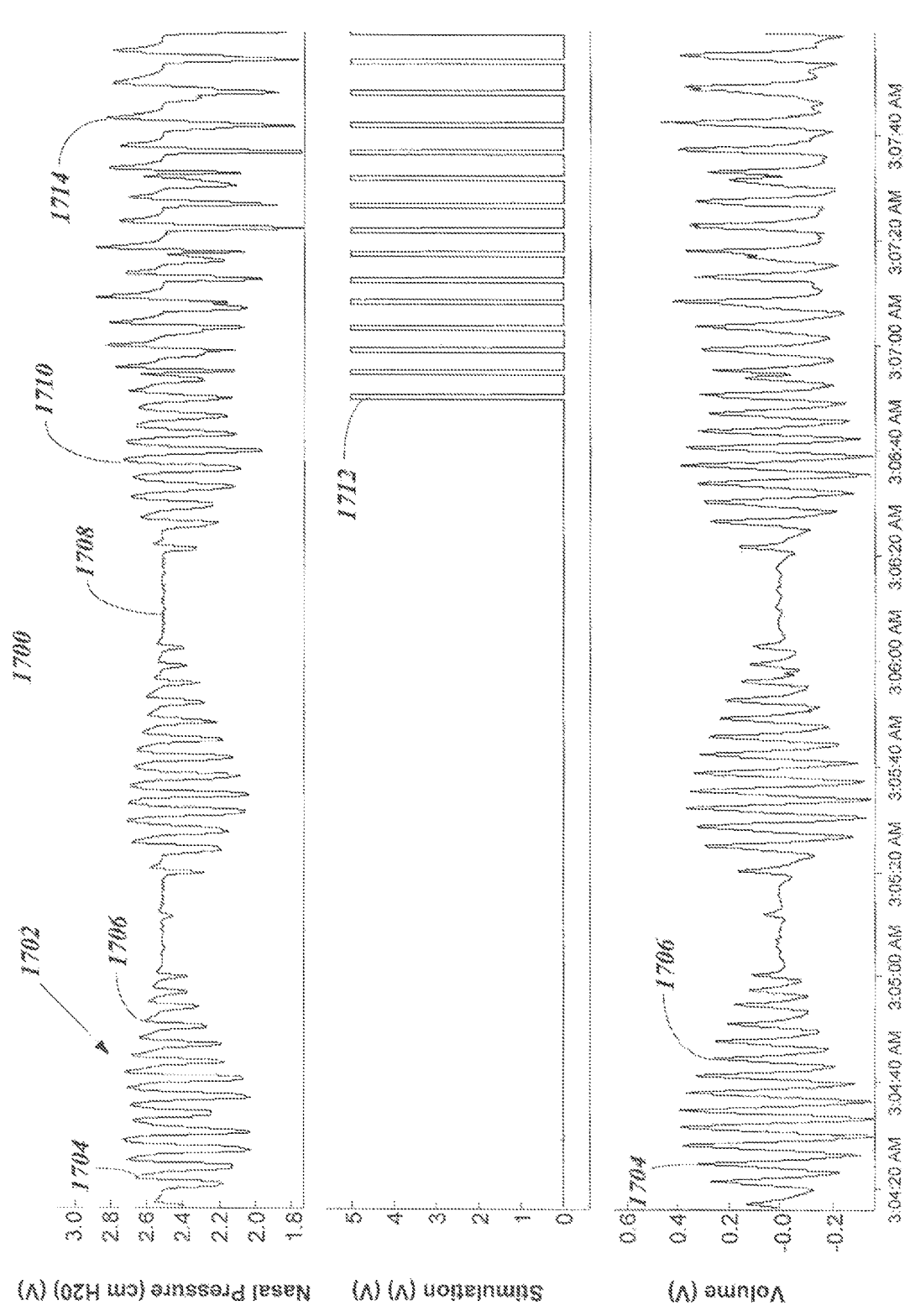
FIG. 17 shows experimental results of treatment of disordered breathing.

FIG. 17 shows experimental results of treatment of disordered breathing carried out in accordance with embodiments of the invention. The patient is experiencing CSR as shown by periods of hyperpnea 1702 and apnea-hypopnea 1708. The hyperpnea exhibits what is commonly referred to as a crescendo 1704-decrescendo 1706 pattern. The patient's breathing rate during the disordered breathing episodes is approximately 18 breaths per minute. Stimulation signals 1712 are initiated during hyperpnea after the midpoint 1710 of the hyperpnea cycle. The stimulation signals extend the breath duration and slow the breathing rate from 18 breaths per minute to 11 breaths per minute. The stimulation signals are applied to additional future breaths 1714 occurring after the normal duration of the hyperpnea cycle. As can be observed, the CSR cycle is broken and the deleterious effects of CSR including, but not limited to, pulse rate variations, blood gas variations, oxygen desaturation are reduced or eliminated. It is believed that long term health benefits will also accrue, particularly for heart failure patients.

The extension of breath duration may not result in a lowered breathing rate as measured by breaths per minute. In cases where, for example, a patient is in hyperpnea for 40 seconds and apnea-hypopnea for 20 seconds, a measured breathing rate of 20 breaths per minute might result from a rate of one breath per two seconds (two-second breaths) during the 40-second hyperpnea with little or no breathing activity during the apnea-hypopnea. Extending the breath duration and eliminating or reducing the apnea-hypopnea may, for example, result in a breathing rate of one breath per three seconds (three-second breaths) over an entire minute, which would still result in a measured breathing rate of 20 breaths per minute.

Figure 18:
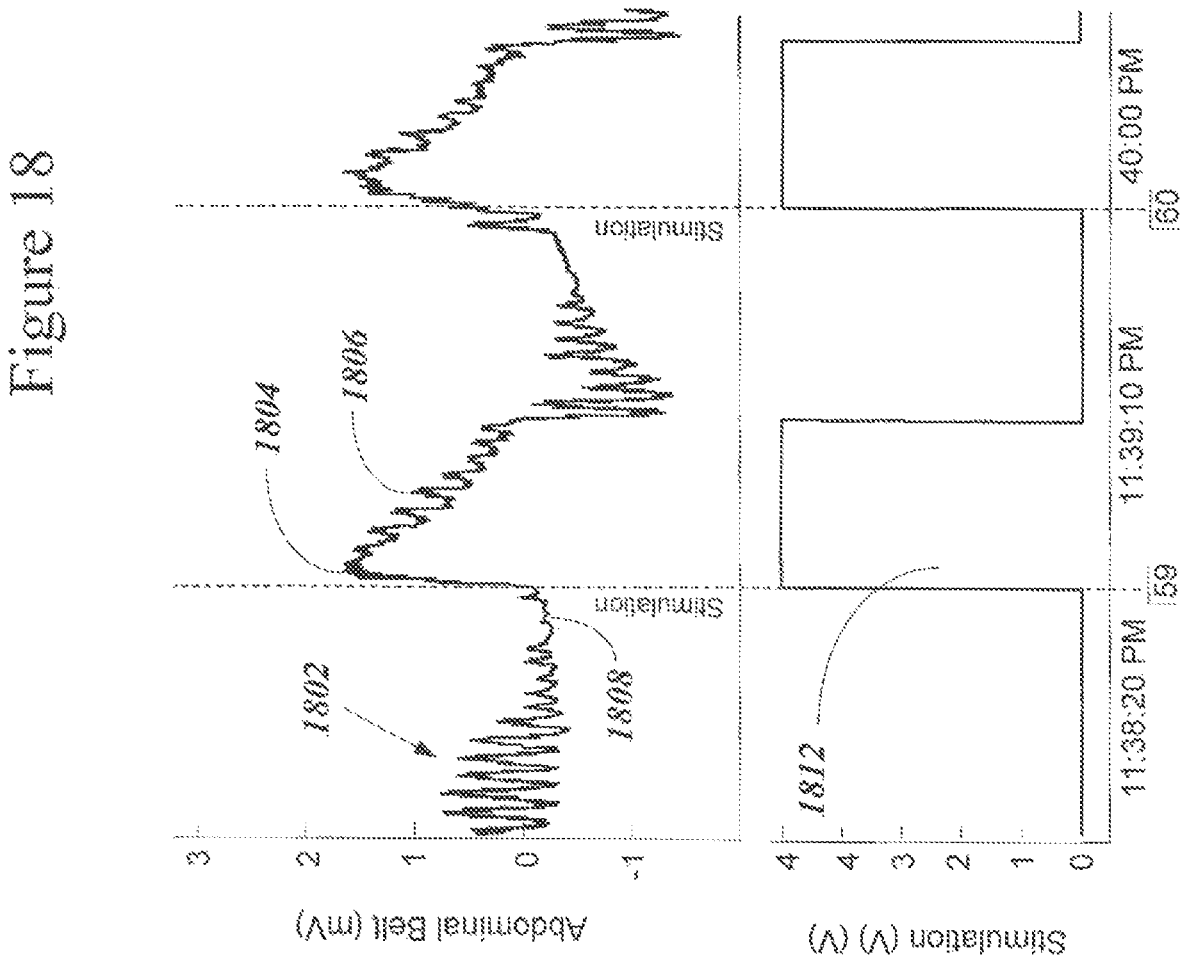
FIG. 18 shows experimental results of treatment of disordered breathing.

FIG. 18 shows experimental results of treatment of disordered breathing carried out in accordance with embodiments of the invention. The patient is experiencing CSR as shown by periods of hyperpnea 1802 and apnea-hypopnea 1808. A stimulation signal 1812 is delivered to one hemidiaphragm at the start of a hyperpnea cycle and the stimulated lung is held open starting at time 1804. The stimulation signal duration is greater than 50% of a normal hyperpnea duration and the stimulated lung is stilled for that entire time. Muted respiration signals 1806 can be seen throughout the stimulation, likely from the contralateral lung still responding to autonomic signals. The stimulation is repeated 1812 at the start of the next hyperpnea until the CSR cycle is broken.

While exemplary embodiments of this invention have been illustrated and described, it should be understood that various changes, adaptations, and modifications may be made therein without departing from the spirit of the invention and the scope of the appended claims.

What is claimed is:

1. A system for treating disordered breathing of a patient comprising:
   an implantable device comprising an energy source, a pulse generator, and associated circuitry and configured to generate a phrenic-nerve stimulation signal in response to a trigger;
   an implantable lead system coupled to the implantable device and configured to transvenously electrically stimulate a phrenic nerve with the phrenic-nerve stimulation signal; and
   sensors communicatively coupled to the implantable device and comprising:
      at least one first sensor configured to provide a respiration signal indicative of patient respiration, and
      at least one second sensor configured to generate a signal indicative of the patient being asleep,
   wherein the implantable device is configured to provide a plurality of selectable treatment modes comprising at least a first treatment mode and a second treatment mode,
   wherein in the first treatment mode, the trigger for the implantable device to generate the phrenic-nerve stimulation signal comprises both the respiration signal and the signal indicative of the patient being asleep, and
   wherein in the second treatment mode, the trigger for the implantable device to generate the phrenic-nerve stimulation signal comprises the signal indicative of the patient being asleep and excludes the respiration signal.

2. The system of claim 1, wherein the at least one second sensor comprises one or more of an accelerometer or a position sensor.

3. The system of claim 1, wherein the at least one first sensor comprises an impedance sensor, an accelerometer, or a pressure sensor.

4. The system of claim 1, wherein the at least one first sensor comprises an external respiration belt.

5. The system of claim 1, wherein the phrenic-nerve stimulation signal is characterized by a duration and comprises a series of current pulses generated for the duration of the phrenic-nerve stimulation signal.

6. The system of claim 5, wherein the implantable device is configured to adjust at least one of the duration or energy of the phrenic-nerve stimulation signal based on the respiration signal.

7. The system of claim 5, wherein the duration of the phrenic-nerve stimulation signal is a duration of at least one breath, the duration of the at least one breath being from an onset of inhalation of a first breath to the onset of inhalation of a successive breath.

8. The system of claim 5, wherein the series of current pulses is generated at a frequency of approximately 20 Hz.

9. The system of claim 5, wherein the series of current pulses is generated with a period of approximately 150 μsec.

10. The system of claim 5, wherein the implantable device is configured to vary a current associated with each of the series of current pulses such that the phrenic-nerve stimulation signal gradually increases from a first current to a second current and gradually decreases from the second current to the first current.

11. The system of claim 10, wherein a range for the second current is about double a range for the first current.

12. The system of claim 11, wherein the range for the first current is about 1-2 mA and the range for the second current is about 2-4 mA.

13. The system of claim 10, wherein the phrenic-nerve stimulation signal gradually rises for approximately 30% of the duration of the phrenic-nerve stimulation signal.

14. The system of claim 10, wherein the phrenic-nerve stimulation signal gradually decreases for approximately 30% of the duration of the phrenic-nerve stimulation signal.

15. The system of claim 10, wherein the gradual increases and decreases of the phrenic-nerve stimulation signal are linear, exponential, parabolic, or combinations thereof.

16. The system of claim 1, wherein in the second treatment mode, the implantable device is configured to generate the phrenic-nerve stimulation signal based on historical data.

17. The system of claim 1, wherein in the first treatment mode, the implantable device is configured to generate the phrenic-nerve stimulation signal in coordination with a mixed apnea respiratory cycle of the patient as indicated by the respiration signal.

18. The system of claim 16, wherein, in the first treatment mode, the implantable device is configured to generate the phrenic-nerve stimulation signal based on the respiration signal being indicative of an apnea-hypopnea period of a respiratory cycle.

19. The system of claim 16, wherein, in the first treatment mode, the implantable device is configured to generate the phrenic-nerve stimulation signal based on the respiration signal being indicative of a hyperpnea period of a respiratory cycle.

20. The system of claim 1, wherein the implantable device is configured to provide the first treatment mode and the second treatment mode in succession.

* * * * *